(12) United States Patent
Miller et al.

(10) Patent No.: US 11,135,340 B2
(45) Date of Patent: Oct. 5, 2021

(54) COMPOSITIONS AND METHODS FOR PREPARATION OF COMPOSITE POLYMER COATINGS ON MEDICAL IMPLANTS, AND THEIR USE FOR CO-DELIVERY OF MULTIPLE ANTIMICROBIAL AGENTS

(71) Applicant: THE JOHNS HOPKINS UNIVERSITY, Baltimore, MD (US)

(72) Inventors: Lloyd S. Miller, Ellicott City, MD (US); Hai-Quan Mao, Baltimore, MD (US); Alyssa Ashbaugh, Baltimore, MD (US); Xuesong Jiang, Lutherville-Timonium, MD (US); Jesse Zheng, Johns Creek, GA (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/076,606

(22) PCT Filed: Feb. 8, 2017

(86) PCT No.: PCT/US2017/016890
§ 371 (c)(1),
(2) Date: Aug. 8, 2018

(87) PCT Pub. No.: WO2017/139301
PCT Pub. Date: Aug. 17, 2017

(65) Prior Publication Data
US 2019/0046688 A1 Feb. 14, 2019

Related U.S. Application Data

(60) Provisional application No. 62/292,635, filed on Feb. 8, 2016.

(51) Int. Cl.
| *A61L 27/34* | (2006.01) |
| *A61L 27/18* | (2006.01) |
| *A61L 27/54* | (2006.01) |
| *A61L 27/04* | (2006.01) |
| *A61L 27/58* | (2006.01) |
| *A61L 27/46* | (2006.01) |
| *A61L 27/32* | (2006.01) |

(52) U.S. Cl.
CPC ............. *A61L 27/34* (2013.01); *A61L 27/04* (2013.01); *A61L 27/18* (2013.01); *A61L 27/32* (2013.01); *A61L 27/46* (2013.01); *A61L 27/54* (2013.01); *A61L 27/58* (2013.01); *A61L 2400/12* (2013.01); *A61L 2420/02* (2013.01); *A61L 2420/08* (2013.01)

(58) Field of Classification Search
CPC .......... A61L 27/34; A61L 27/46; A61L 27/18; A61L 27/32; A61L 27/04; A61L 27/54; A61L 27/58; A61L 2400/12; A61L 2420/12; A61L 2420/02
See application file for complete search history.

(56) References Cited

U.S. PATENT DOCUMENTS

| 7,824,699 B2 | 11/2010 | Ralph et al. |
| 9,125,811 B2* | 9/2015 | Tojo .................... A61K 8/0208 |
| 2012/0058100 A1 | 3/2012 | Shastri et al. |
| 2013/0156935 A1 | 6/2013 | Ohri et al. |
| 2014/0037708 A1 | 2/2014 | Tan et al. |
| 2014/0127392 A1* | 5/2014 | Berckmans, III ...... A61C 13/00 427/2.27 |
| 2014/0358217 A1 | 12/2014 | Stankus et al. |
| 2015/0290354 A1 | 10/2015 | Loboa et al. |

OTHER PUBLICATIONS

Blakney, Anna K., et al. "Delivery of multipurpose prevention drug combinations from electrospun nanofibers using composite microarchitectures." International journal of nanomedicine 9 (2014): 2967-2978.*
Gilchrist, Samuel E., et al. "Fusidic acid and rifampicin co-loaded PLGA nanofibers for the prevention of orthopedic implant associated infections." Journal of controlled release 170.1 (2013): 64-73.*
Soujanya, G. Keerthi, et al. "Electrospun nanofibrous polymer coated magnesium alloy for biodegradable implant applications." Procedia Materials Science 5 (2014): 817-823.*
Wang, Shige, et al. "Electrospun hybrid nanofibers doped with nanoparticles or nanotubes for biomedical applications." Therapeutic delivery 3.10 (2012): 1155-1169.*
Gunn, Jonathan, and Miqin Zhang. "Polyblend nanofibers for biomedical applications: perspectives and challenges." Trends in biotechnology 28.4 (2010): 189-197.*
Tan, Eunice PS, and C. T. Lim. "Effects of annealing on the structural and mechanical properties of electrospun polymeric nanofibres." Nanotechnology 17.10 (2006): 2649-2654.*
International Search Report and Written Opinion dated May 19, 2017, from related PCT Patent Application No. PCT/US2017/016890.
Ashbaugh et al., Polymeric nanofiber coating with tunable combinatorial antibiotic delivery prevents biofilm-associated infection in vivo. Proc Natl Acad Sci U S A. Nov. 8, 2016;113(45):E6919-E6928.
Baddour et al., Clinical practice. Infections of cardiovascular implantable electronic devices. N Engl J Med. Aug. 30, 2012;367(9):842-9.
Bjarnsholt et al., Applying insights from biofilm biology to drug development—can a new approach be developed? Nat Rev Drug Discov. Oct. 2013;12(10):791-808.

(Continued)

*Primary Examiner* — Bethany P Barham
*Assistant Examiner* — Peter Anthopolos
(74) *Attorney, Agent, or Firm* — Jeffrey W. Childers

(57) ABSTRACT

The presently disclosed subject matter provides a coating composition which allows for the co-delivery of two or more bioactive agents with independent control of loading level and release profile for each bioactive agent, an implantable medical device coated with the coating composition, and methods for preparing the coating composition.

32 Claims, 24 Drawing Sheets
(23 of 24 Drawing Sheet(s) Filed in Color)

(56) References Cited

OTHER PUBLICATIONS

Bye et al., Postproduction processing of electrospun fibres for tissue engineering. J Vis Exp. Aug. 9, 2012;(66). pii: 4172.

Campoccia et al., A review of the biomaterials technologies for infection-resistant surfaces. Biomaterials. Nov. 2013;34(34):8533-54.

Costerton et al., Bacterial biofilms: a common cause of persistent infections. Science. May 21, 1999;284(5418):1318-22.

Darouiche, Treatment of infections associated with surgical implants. N Engl J Med. Apr. 1, 2004;350(14):1422-9.

Del Pozo et al., Clinical practice. Infection associated with prosthetic joints. N Engl J Med. Aug. 20, 2009;361(8):787-94.

Francis et al., Monitoring bioluminescent *Staphylococcus aureus* infections in living mice using a novel luxABCDE construct. Infect Immun. Jun. 2000;68(6):3594-600.

Goodman et al., The future of biologic coatings for orthopaedic implants. Biomaterials. Apr. 2013;34(13):3174-83.

Hall-Stoodley et al., 2004. Bacterial biofilms: from the natural environment to infectious diseases. Nat Rev Microbiol. Feb. 2004;2(2):95-108.

Kurtz et al., Future clinical and economic impact of revision total hip and knee arthroplasty. J Bone Joint Surg Am. Oct. 2007;89 Suppl 3:144-51.

Kurtz et al., Infection burden for hip and knee arthroplasty in the United States. J Arthroplasty. Oct. 2008;23(7):984-91.

Kurtz et al., Projections of primary and revision hip and knee arthroplasty in the United States from 2005 to 2030. J Bone Joint Surg Am. Apr. 2007;89(4):780-5.

Liu et al., Clinical practice guidelines by the Infectious Diseases Society of America for the treatment of methicillin-resistant *Staphylococcus aureus* infections in adults and children. Clin Infect Dis. Feb. 1, 2011;52(3):e18-55.

Liu et al., Solvent vapor annealing: an efficient approach for inscribing secondary nanostructures onto electrospun fibers. Macromol Rapid Commun. Sep. 2014;35(17):1503-8.

Lora-Tamayo et al., A Large Multicenter Study of Methicillin-Susceptible and Methicillin-Resistant *Staphylococcus aureus* Prosthetic Joint Infections Managed with Implant Retention. Clin Infect Dis. Jan. 2013;56(2):182-94.

Niska et al., Daptomycin and tigecycline have broader effective dose ranges than vancomycin as prophylaxis against a *Staphylococcus aureus* surgical implant infection in mice. Antimicrob Agents Chemother. May 2012;56(5):2590-7.

Ordonez et al., Radioiodinated DPA-713 imaging correlates with bactericidal activity of tuberculosis treatments in mice. Antimicrob Agents Chemother. Jan. 2015;59(1):642-9.

Osmon et al., Diagnosis and management of prosthetic joint infection: clinical practice guidelines by the Infectious Diseases Society of America. Clin Infect Dis. Jan. 2013;56(1):e1-e25.

Pribaz et al., Mouse model of chronic post-arthroplasty infection: noninvasive in vivo bioluminescence imaging to monitor bacterial burden for long-term study. J Orthop Res. Mar. 2012;30(3):335-40.

Raad et al., Comparative activities of daptomycin, linezolid, and tigecycline against catheter related methicillin-resistant *Staphylococcus* bacteremic isolates embedded in biofilm. Antimicrob Agents Chemother. May 2007;51(5):1656-60.

Saginur et al., Multiple combination bactericidal testing of staphylococcal biofilms from implant associated infections. Antimicrob Agents Chemother. Jan. 2006;50(1):55-61.

Sandoe et al., Guidelines for the diagnosis, prevention and management of implantable cardiac electronic device infection. Report of a joint Working Party project on behalf of the British Society for Antimicrobial Chemotherapy (BSAC, host organization), British Heart Rhythm Society (BHRS), British Cardiovascular Society (BCS), British Heart Valve Society (BHVS) and British Society for Echocardiography (BSE). J Antimicrob Chemother. Feb. 2015;70(2):325-59.

Senneville et al., Outcome and predictors of treatment failure in total hip/knee prosthetic joint infections due to *Staphylococcus aureus*. Clin Infect Dis. Aug. 2011;53(4):334-40.

Song et al., Coaxial PCL/PVA electrospun nanofibers: osseointegration enhancer and controlled drug release device. Biofabrication. Sep. 2013;5(3):03500.

Zhang et al., Electrospun vancomycin-loaded coating on titanium implants for the prevention of implant-associated infections. Int J Nanomedicine. Jun. 23, 2014;9:3027-36.

Zimmerli et al., Prosthetic-joint infections. N Engl J Med. Oct. 14, 2004;351(16):1645-54.

Extended European Search Report for EP 17750651.6, dated Sep. 26, 2019, 9 pages.

Abdal-Hay et al., In vitro bioactivity of titanium implants coated with biocomponent hybrid biodegradable polymers. J Sol-Gel Sci Technol. 2012;64:756-64.

\* cited by examiner

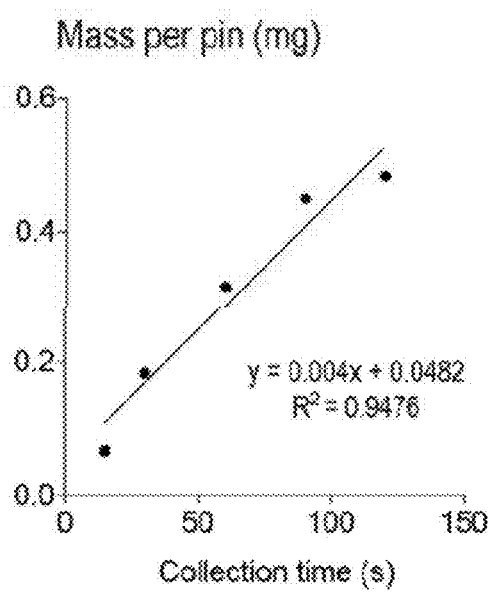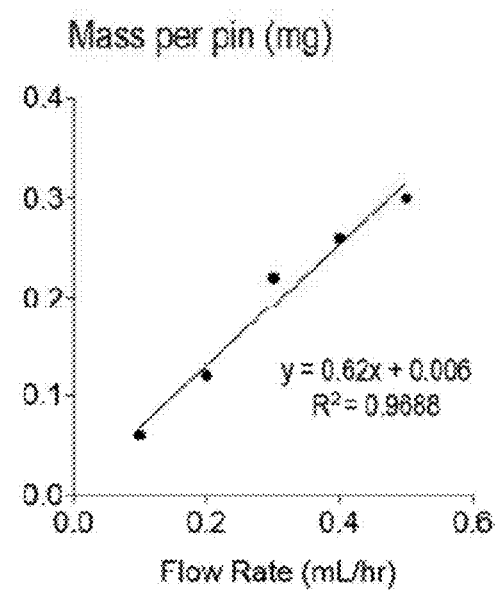
*Fig. 2A*  *Fig. 2B*

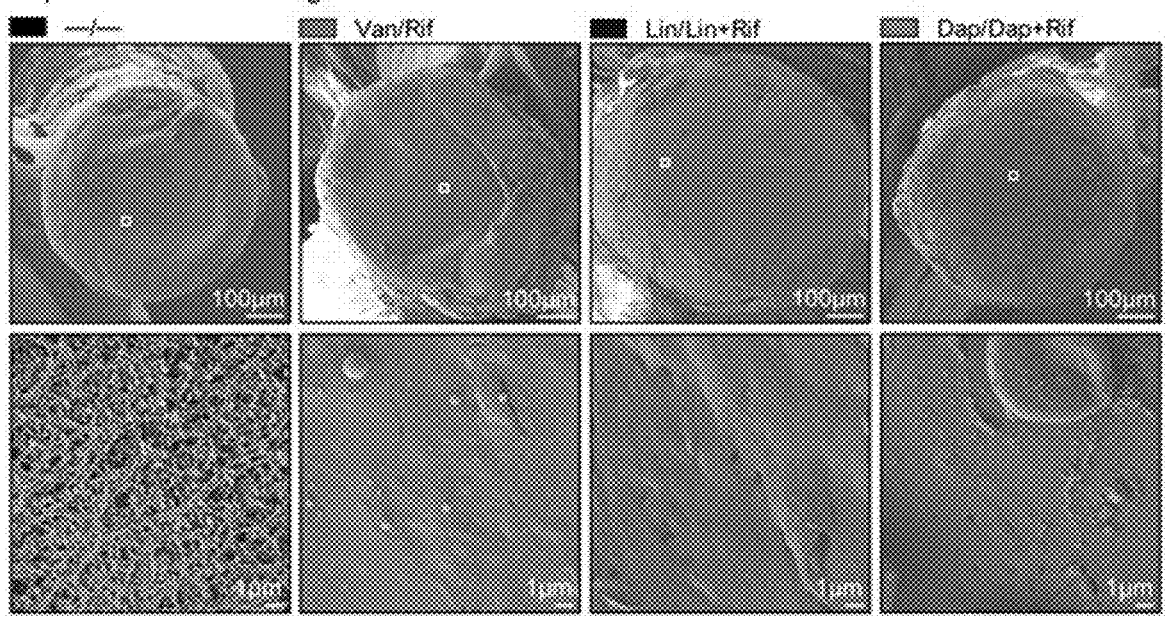
*Fig. 6A*  *Fig. 6B*  *Fig. 6C*  *Fig. 6D*

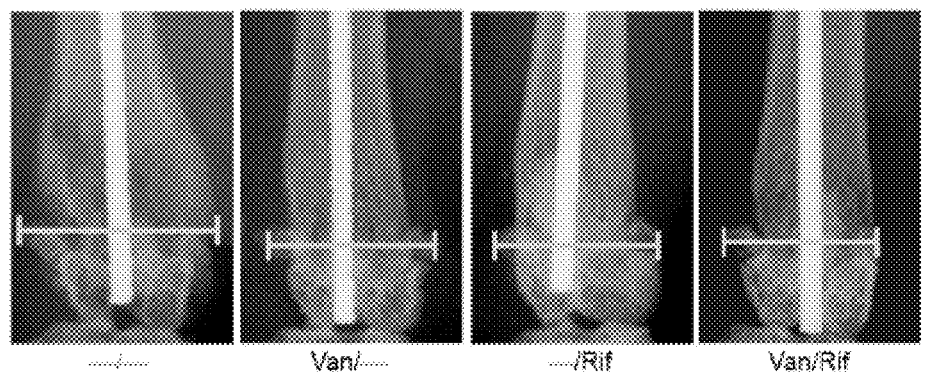
*Fig. 7A*
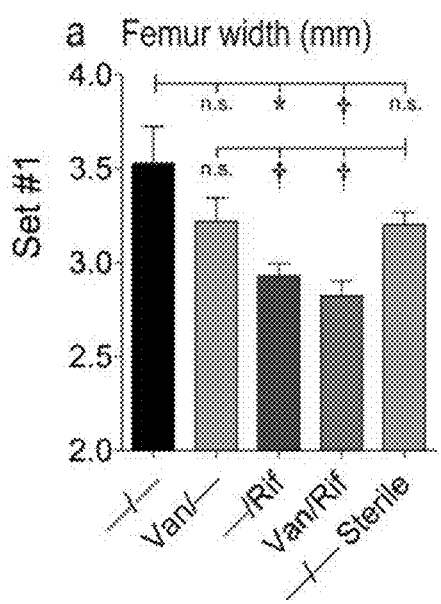 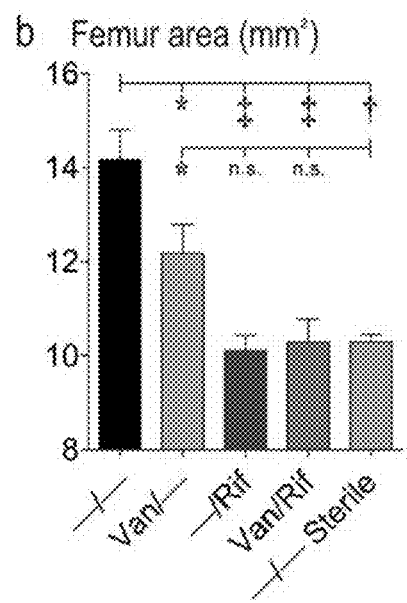
*Fig. 7B*     *Fig. 7C*

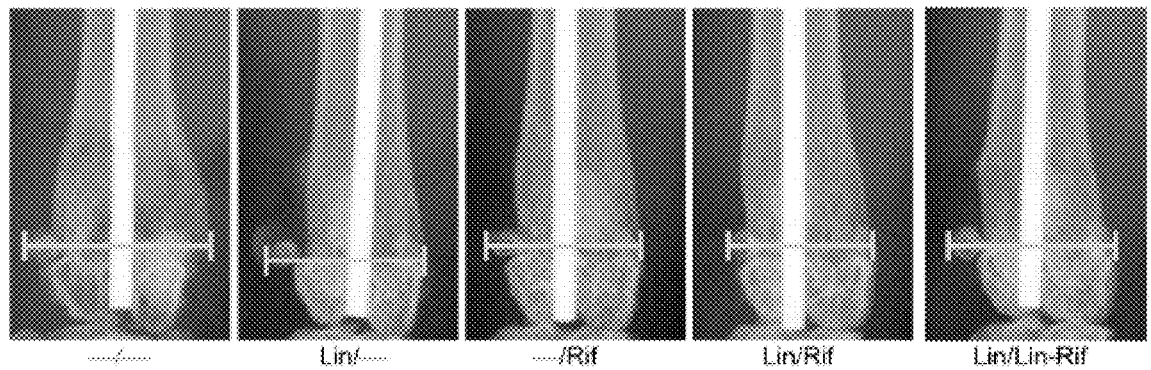
*Fig. 7D*
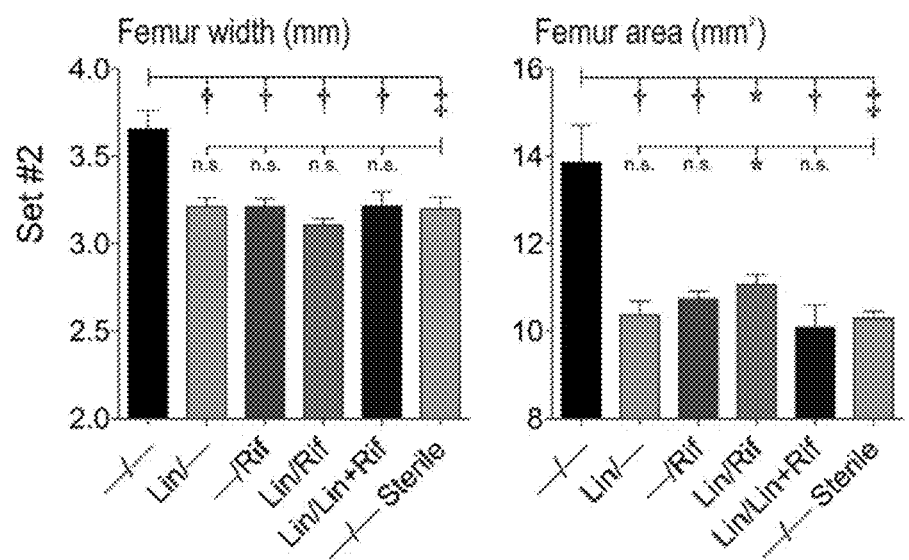
*Fig. 7E*  *Fig. 7F*

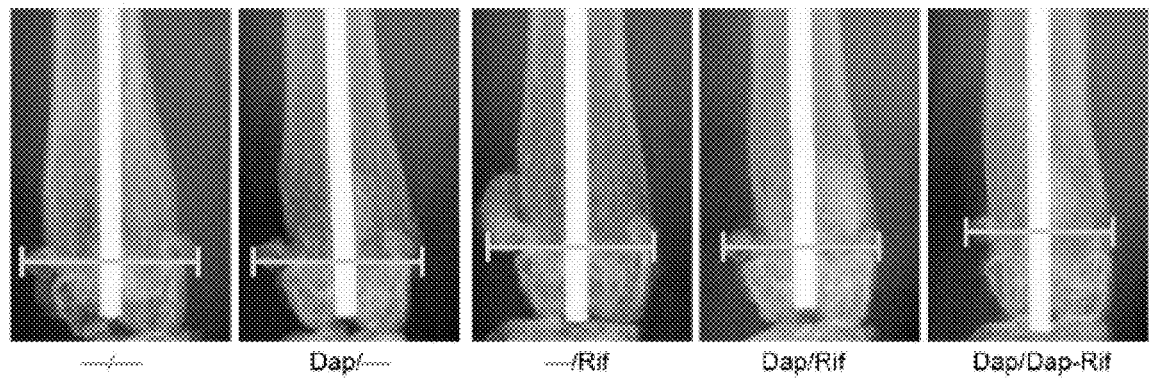
*Fig. 7G*
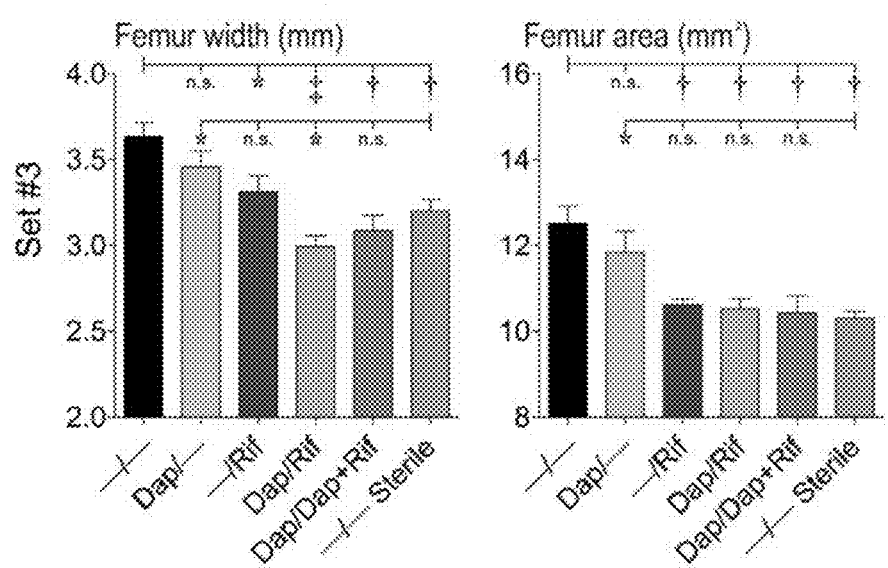
*Fig. 7H*     *Fig. 7I*

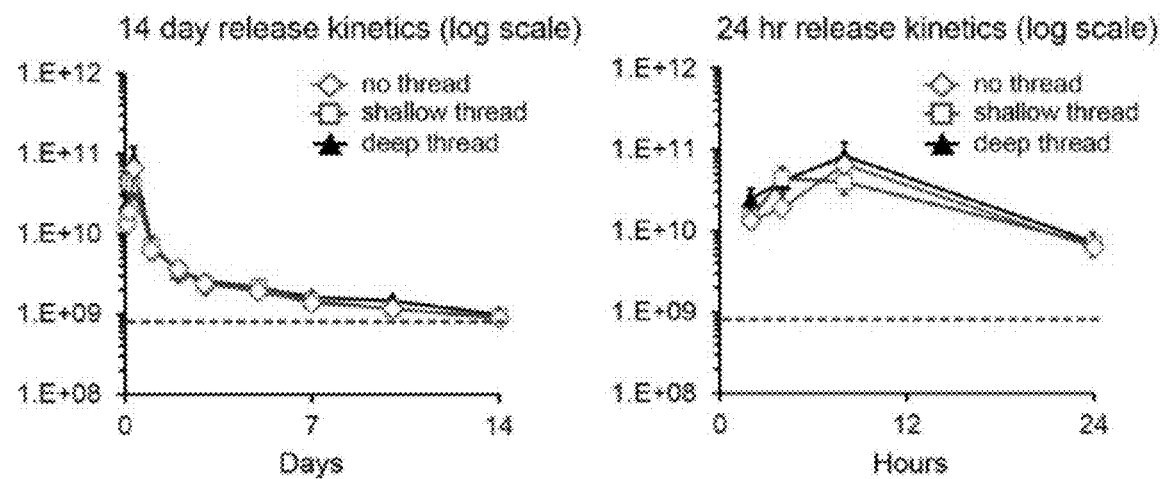
*Fig. 9A*
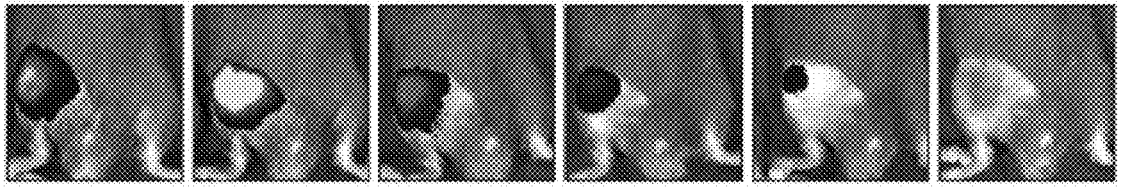
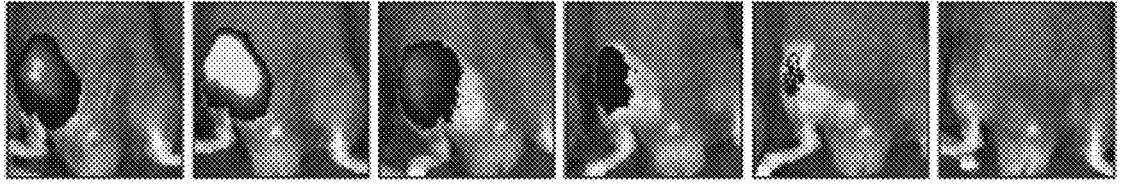
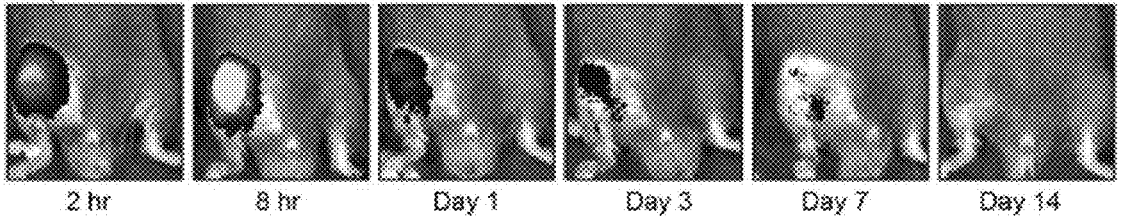
*Fig. 9B*

COMPOSITIONS AND METHODS FOR PREPARATION OF COMPOSITE POLYMER COATINGS ON MEDICAL IMPLANTS, AND THEIR USE FOR CO-DELIVERY OF MULTIPLE ANTIMICROBIAL AGENTS

CROSS-REFERENCE TO RELATED APPLICATIONS

This application is a 35 U.S.C. § 371 National Stage Entry of International Application No. PCT/US2017/016890 having an international filing date of Feb. 8, 2017, which claims the benefit of U.S. Provisional Application No. 62/292,635, filed Feb. 8, 2016, the contents of which are incorporated herein by reference in their entirety.

FEDERALLY SPONSORED RESEARCH OR DEVELOPMENT

This invention was made with government support under UL1TR001079 awarded by the National Center for Advancing Translational Sciences (NCATS) of the U.S. National Institutes of Health (NIH) and NIH Roadmap for Medical Research. The government has certain rights in the invention.

BACKGROUND

Infection is a devastating complication and a major impediment to the success of implanted medical devices (Darouiche, 2004), such as orthopedic prostheses (Del Pozo et al., 2009, Zimmerli et al., 2004) and cardiac implantable electrophysiological devices (CIED) (e.g., pacemakers and cardioverters-defibrillators) (Baddour et al., 2012). In particular, prosthetic joint infection (PJI) represents one of the most devastating complications of total knee and hip replacement surgery and is one of the leading causes of arthroplasty failure. The current standard of care in preventing this infection is perioperative prophylactic systemic antibiotics. Despite this effort, the rate of deep infection after total joint arthroplasty is as high as 1-4% (Kurtz et al., 2008), which corresponds to nearly 20,000 post-arthroplasty infections in the U.S. each year. This number is expected to rise, by approximately over 35,000 cases each year by 2030 (Kurtz, Ong, Lau et al., 2007; Kurtz, Ong, Schmier et al., 2007). For CIED, the percentage of infections is rising at faster rate than the expected number of infections based on the increasing numbers of CIED implanted (Baddour et al., 2012). There are 2 million fracture-fixation devices implanted each year in the U.S. (e.g., external-fixation devices, intramedullary nails, plates and screws) that result in 100,000 infections (Darouiche, 2004).

Bacteria adhere to and colonize the surface of implanted medical devices, leading to the formation of a biofilm, an assemblage of microorganisms associated with surfaces and a dense network of extracellular matrix. Biofilms can protect the bacteria from the immune system and decrease their susceptibility to antibiotics, thereby creating a chronic and persistent infection (Costerton et al., 1999; Hall-Stoodley et al., 2004).

As a result, antimicrobial therapy is often unsuccessful unless the biofilm is physically disrupted or removed by surgical debridement (Darouiche, 2004). The management of PJIs, CIED infections and other medical device infections generally involves both surgical intervention and prolonged antibiotic therapy, imposing a substantial economic burden on health care systems (Osmon et al., 2013, Sandoe et al. 2015). Therefore, there has been a great deal of interest in devising strategies to minimize biofilm formation on medical devices to prevent these infections.

SUMMARY

In one aspect, the presently disclosed subject matter provides a method for coating an implantable medical device with a conformal coating comprising at least a first bioactive agent, the method comprising: (a) depositing onto at least a portion of a metallic surface of an implantable medical device using electrospinning: (i) a plurality of polymer nanofibers, wherein the plurality of polymer nanofibers comprise at least a first set of polymer nanofibers with a melting temperature of about 40° C. to about 100° C. and at least a second set of polymer nanofibers with a higher melting temperature than the melting temperature of the first set of polymer nanofibers; and (ii) at least a first bioactive agent loaded into the first set of polymer nanofibers and/or the second set of polymer nanofibers; (b) annealing the implantable medical device for a controlled time period at a controlled temperature that is higher than the melting temperature of the first set of polymer nanofibers; and (c) cooling the implantable device to form a solid coating comprising the plurality of polymer nanofibers and the first bioactive agent; thereby coating the implantable medical device with the conformal coating comprising the first bioactive agent.

In certain aspects, annealing the implantable medical device occurs at a controlled temperature that is from about 10° C. to about 20° C. higher than the melting temperature of the first set of polymer nanofibers. In some aspects, annealing occurs at a controlled temperature that is from about 50° C. to about 80° C.

In other aspects, step (a) is repeated to deposit at least a third set of polymer nanofibers and either the first bioactive agent and/or at least a second bioactive agent onto at least the portion of the metallic surface of the implantable medical device. In some aspects, the controlled temperature does not significantly reduce the bioactivity of the first bioactive agent and/or the second bioactive agent. In some aspects, the loading level of at least one of the first bioactive agent or second bioactive agent in the first set of polymer nanofibers and/or second set of polymer nanofibers is from about 1% to about 50%. In some aspects, the controlled time period is from about 10 seconds to about 20 minutes.

In certain aspects, the presently disclosed subject matter provides a coating composition comprising: (a) a polymer film produced from a first set of polymer nanofibers with a first capacity for loading of at least a first bioactive agent that is released in vivo at a first release rate; (b) at least a second set of polymer nanofibers embedded in the polymer film, wherein the second set of polymer nanofibers comprise at least a second capacity for loading of at least one of the first bioactive agent or at least a second bioactive agent that is released in vivo at a second release rate, wherein the first capacity for loading of the first bioactive agent in the polymer film is independent of the second capacity for loading of the at least one of the first bioactive agent or second bioactive agent, and wherein the first release rate of the first bioactive agent in vivo from the polymer film is independent of the second release rate of the at least one of the first bioactive agent or second bioactive agent in vivo from the at least a second set of polymer nanofibers; and (c) at least one of the first bioactive agent or second bioactive agent loaded in the polymer film and/or in the second set of polymer nanofibers.

In other aspects, the presently disclosed subject matter provides an implantable medical device comprising: (a) a metallic surface; and (b) a conformal coating on at least a portion of the metallic surface, the conformal coating comprising: (i) a polymer film produced from a first set of polymer nanofibers with a first capacity for loading of at least a first bioactive agent that is released in vivo at a first release rate; (ii) at least a second set of polymer nanofibers embedded in the polymer film, wherein the second set of polymer nanofibers comprise at least a second capacity for loading of at least one of the first bioactive agent or at least a second bioactive agent that is released in vivo at a second release rate, wherein the first capacity for loading of the first bioactive agent in the polymer film is independent of the second capacity for loading of the at least one of the first bioactive agent or second bioactive agent, and wherein the first release rate of the first bioactive agent in vivo from the polymer film is independent of the second release rate of the at least one of the first bioactive agent or second bioactive agent in vivo from the at least a second set of polymer nanofibers; and (iii) at least one of the first bioactive agent or second bioactive agent loaded in the polymer film and/or in the second set of polymer nanofibers.

In yet other aspects, the second set of polymer nanofibers is loaded with the first bioactive agent. In some aspects, the polymer film is loaded with the first bioactive agent. In some aspects, the second set of polymer nanofibers and the polymer film are each loaded with either the first bioactive agent or the second bioactive agent. In some aspects, the method, coating composition, or device further comprises at least a third set of polymer nanofibers, wherein the polymer film is loaded with the first bioactive agent, the second set of polymer nanofibers is loaded with the second bioactive agent, and the third set of polymer nanofibers is loaded with at least a third bioactive agent, wherein the first bioactive agent, the second bioactive agent, and the third bioactive agent are each different bioactive agents.

In further aspects, the coating composition releases the first bioactive agent and the second bioactive agent simultaneously and in a controlled manner, wherein the first bioactive agent is released from the polymer film and the second bioactive agent is released from the second set of polymer nanofibers. In some aspects, the coating composition releases the first bioactive agent and the second bioactive agent simultaneously and immediately in a controlled manner, wherein the first bioactive agent is released from the polymer film and the second bioactive agent is released from the second set of polymer nanofibers. In some aspects, the coating composition releases the first bioactive agent and the second bioactive agent simultaneously and immediately at different release rates in a controlled manner. In some aspects, the coating composition releases the first bioactive agent and the second bioactive agent simultaneously and immediately at different release rates in a controlled manner, wherein the first bioactive agent is released from the polymer film and the second bioactive agent is released from the second set of polymer nanofibers. In some aspects, the coating composition releases the first bioactive agent, the second bioactive agent, and/or the third bioactive agent over a time period of about three days to about four weeks.

In some aspects, the first set of polymer nanofibers, the second set of polymer nanofibers, and the third set of polymer nanofibers each comprise a different homopolymer or copolymer. In some aspects, the first set of polymer nanofibers, the second set of polymer nanofibers, and the third set of polymer nanofibers each comprise a homopolymer or copolymer of monomers selected from the group consisting of ε-caprolactone, D-lactide, L-lactide, and glycolide. In some aspects, the first set of polymer nanofibers comprises a polymer that is selected from the group consisting of poly(ε-caprolactone), a copolymer of ε-caprolactone and d-lactide, a copolymer of ε-caprolactone and 1-lactide, and a copolymer of ε-caprolactone and glycolide. In some aspects, the first set of polymer nanofibers comprises poly(ε-caprolactone). In some aspects, the second set of polymer nanofibers and/or the third set of polymer nanofibers comprise poly(D,L-lactide-co-glycolide). In some aspects, the first set of polymer nanofibers comprises poly(ε-caprolactone), and the second set of polymer nanofibers and/or the third set of polymer nanofibers comprise poly(D,L-lactide-co-glycolide).

In certain aspects, the first bioactive agent, the second bioactive agent, and/or the third bioactive agent is an antibiotic. In some aspects, the antibiotic is selected from the group consisting of rifampin, linezolid, vancomycin and daptomycin. In some aspects, the coating composition comprises: (a) linezolid loaded in the second set of polymer nanofibers, and linezolid and rifampin loaded in the polymer film; or (b) daptomycin loaded in the second set of polymer nanofibers, and daptomycin and rifampin loaded in the polymer film; or (c) vancomycin loaded in the second set of polymer nanofibers and rifampin loaded in the polymer film.

In other aspects the plurality of nanofibers has an average diameter from about 50 nm to about 10 μm. In some aspects, the polymer film has an average thickness from about 20 μm to about 500 μm. In some aspects, the coating composition is biodegradable. In some aspects, the weight ratio of the at least second set of polymer nanofibers and the polymer film is from about 80:20 to about 10:90. In some aspects, the weight ratio of poly(D,L-lactide-co-glycolide) to poly(ε-caprolactone) is from about 80:20 to about 10:90. In some aspects, the polymer film further comprises hydroxyapatite nanocrystals.

In some aspects, the first bioactive agent, the second bioactive agent, and/or the third bioactive agent are selected from the group consisting of a polypeptide, growth factor, a steroid agent, a therapeutic antibody, an antibody fragment, a DNA, an RNA, and siRNA, an antimicrobial agent, an antibiotic, an anti-retroviral agent, an anti-inflammatory agent, an anti-tumor agent, anti-angiogenic agent, and a chemotherapeutic agent.

In some aspects, the implantable medical device is an orthopedic device, a dental device, a cardiovascular device, a neurological device, a neurovascular device, a gastrointestinal device, a muscular device, an intramedullary device, or an ocular device. In some aspects, the implantable medical device is an artificial joint, an internal fracture-fixation device, an external fracture-fixation device, a device for fixation of small bones, a device for fixation of the spine, a pacemaker, an implantable cardioverter-defibrillator, a stent, a nail, a rod, a screw, a plate, a clip, or a pin.

In some aspects, the conformal coating inhibits at least one genus of bacteria. In some aspects, the genus of bacteria is selected from the group consisting of *Staphylococcus, Acinetobacter, Klebsiella, Enterococcus, Streptococcus, Escherichia, Proteus, Pseudomonas, Propionibacterium* and *Vibrio*.

In some aspects, the presently disclosed subject matter provides a method for reducing or preventing the formation of a biofilm in vivo after implantation of an implantable medical device into a patient, the method comprising implanting an implantable medical device comprising a metallic surface into a patient, wherein at least a portion of the metallic surface is coated with a conformal coating comprising: (a) a polymer film produced from a first set of polymer nanofibers; (b) at least a second set of polymer nanofibers; and (c) at least two different antibiotic agents loaded into the polymer film and/or the at least second set of polymer nanofibers; wherein upon implantation of the implantable medical device into the patient, the at least two different antibiotic agents are simultaneously and immediately released at different, independent release profiles, thereby reducing or preventing the formation of the biofilm in vivo.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

The patent or application file contains at least one drawing executed in color. Copies of this patent or patent application publication with color drawings will be provided by the Office upon request and payment of the necessary fee.

Figure 1A:
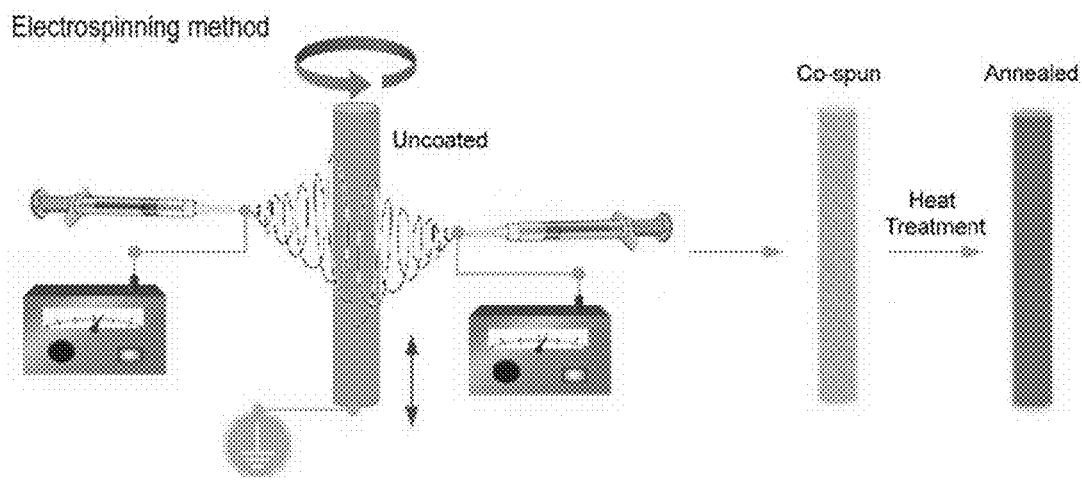
Figure 1E:
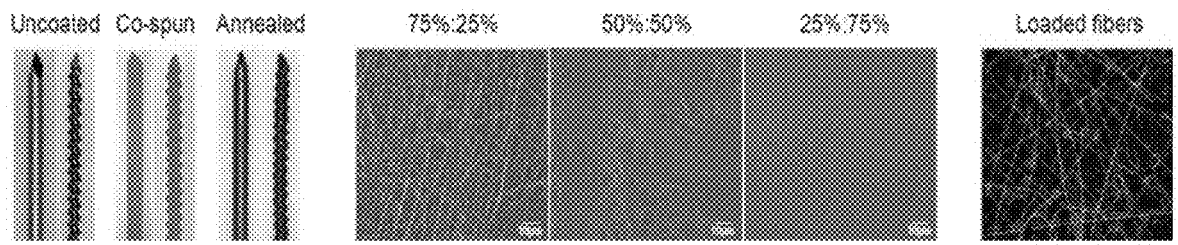
Figure 3A:
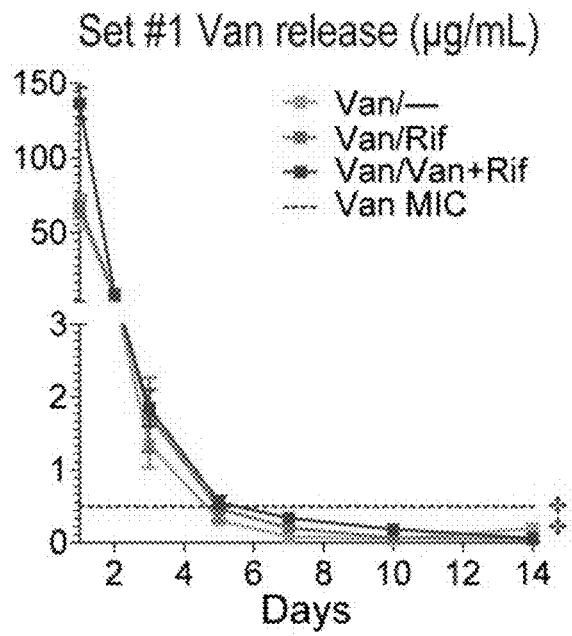
Figure 3B:
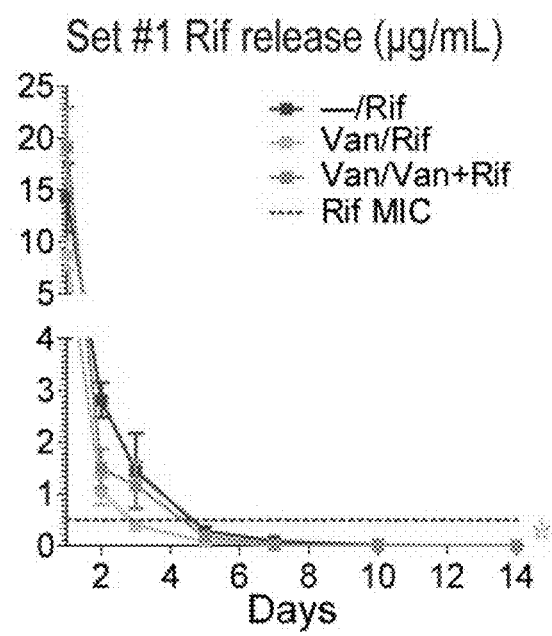
Figure 3C:
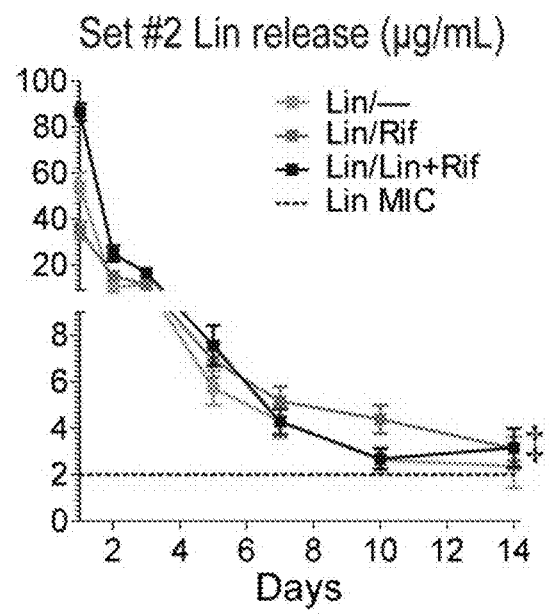
Figure 3D:
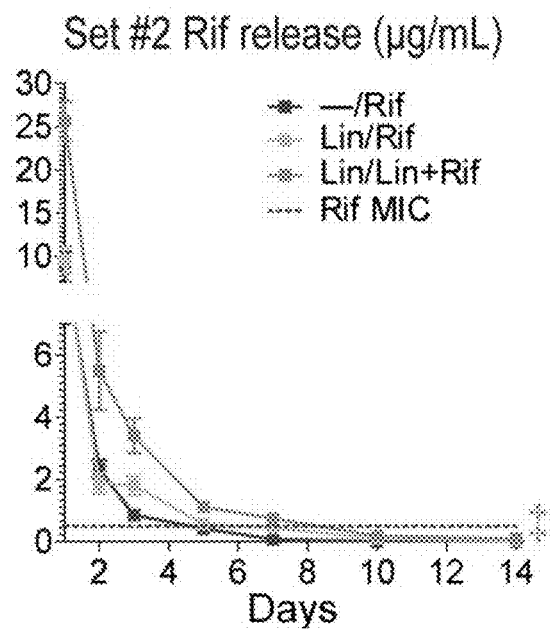
Figure 3E:
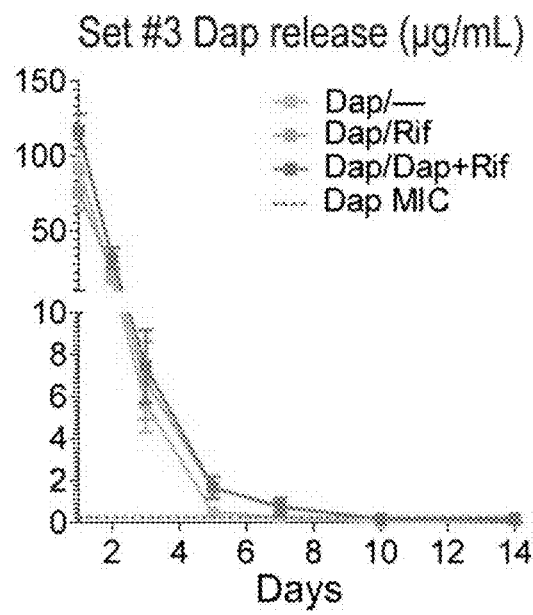
Figure 3F:
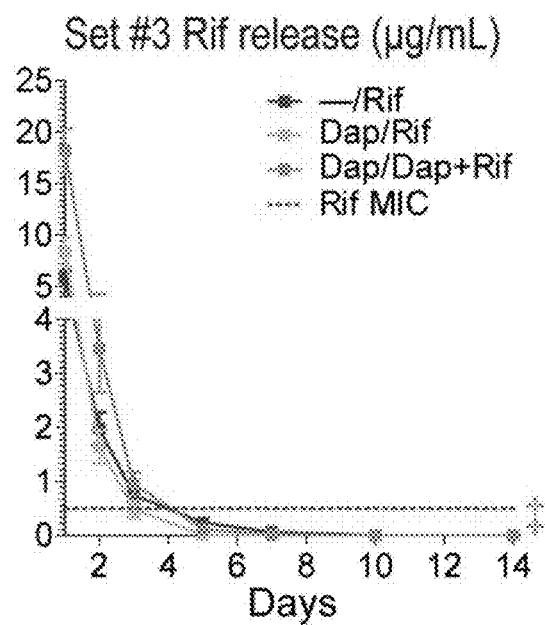
Figure 4A:
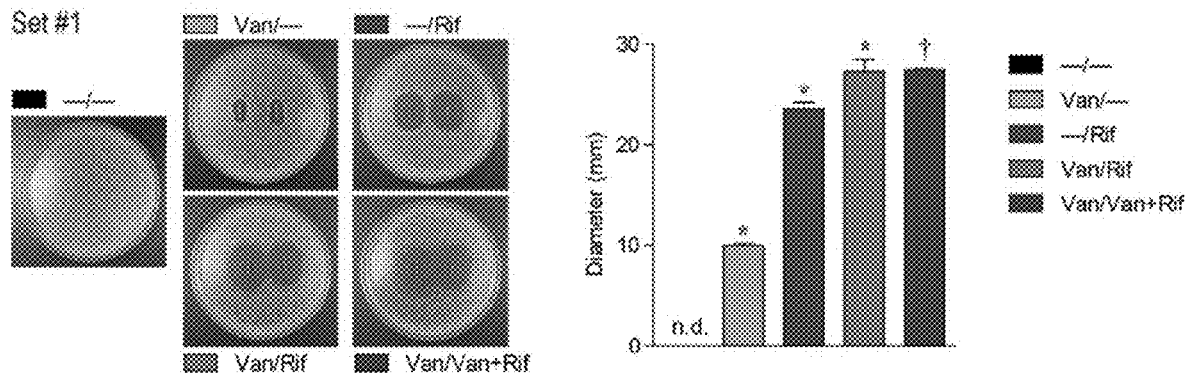
Figure 4B:
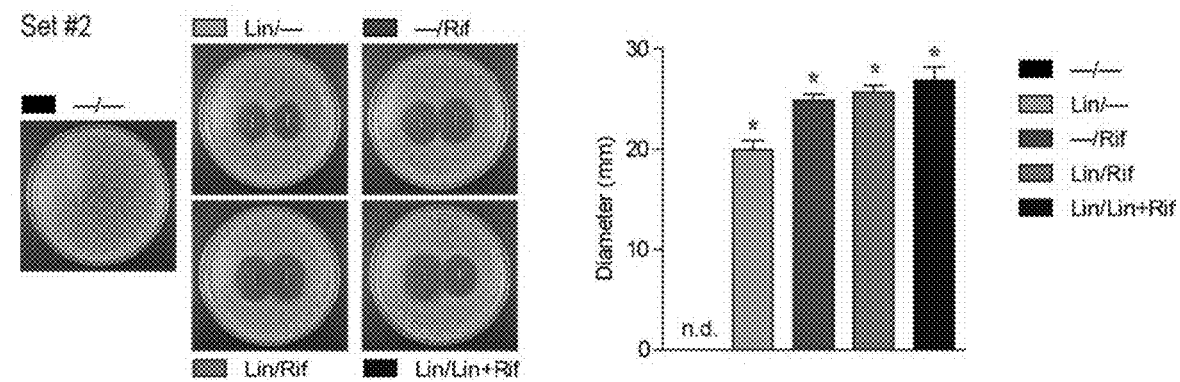
Figure 4C:
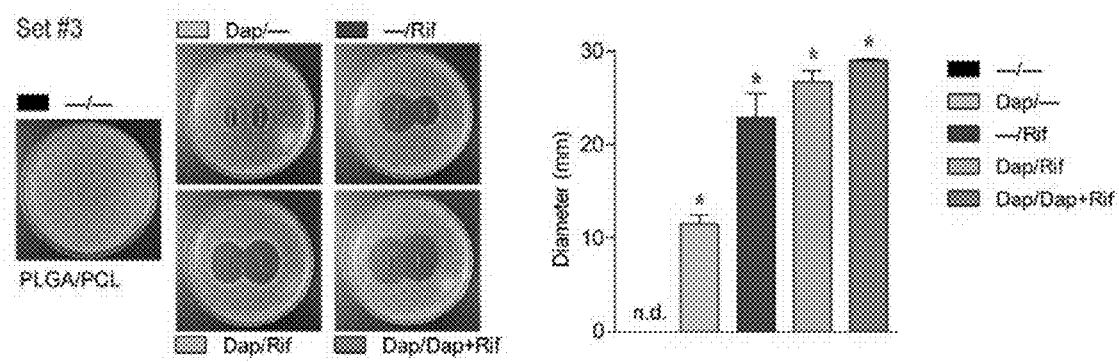
Figure 5A:
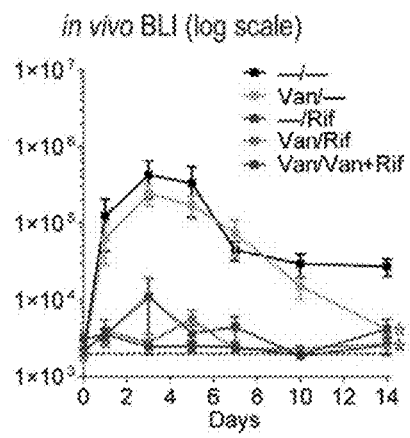
Figure 5B:
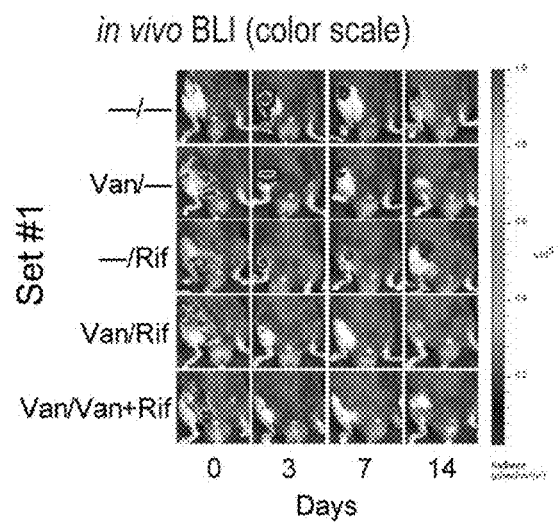
Figure 5C:
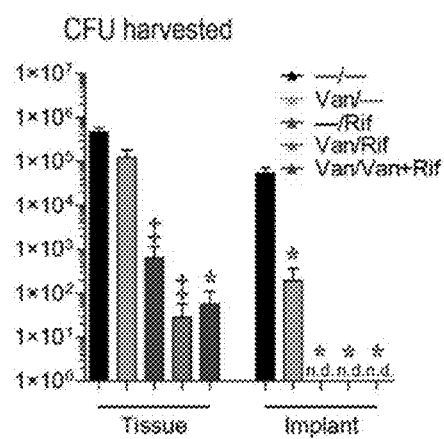
Figure 5D:
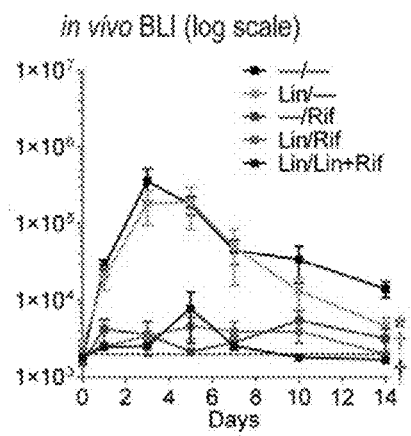
Figure 5E:
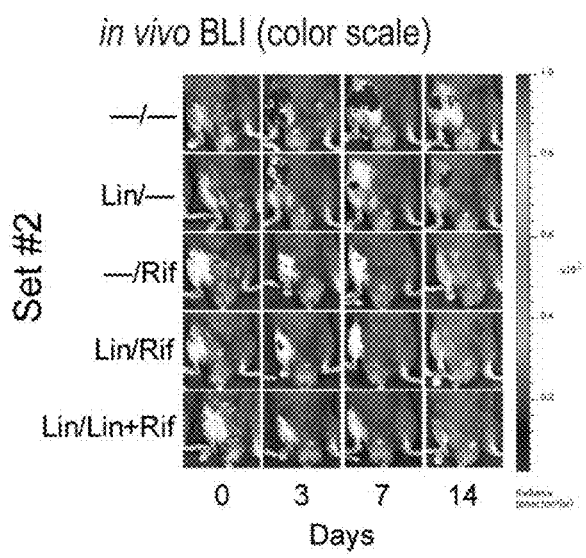
Figure 5F:
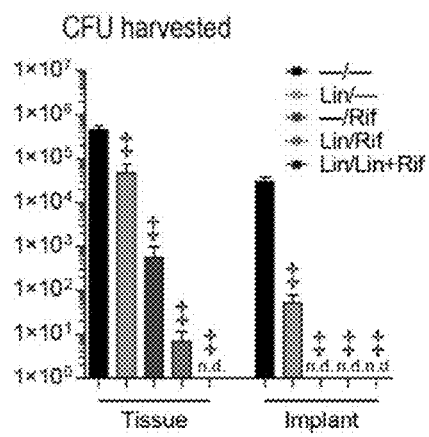
Figure 5G:
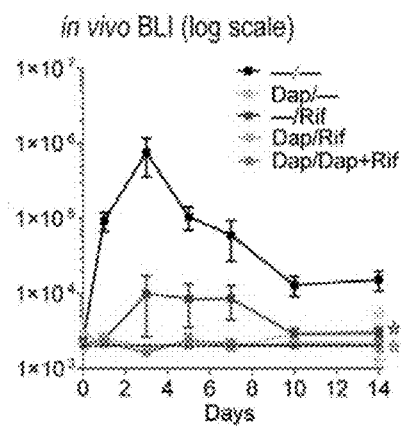
Figure 5H:
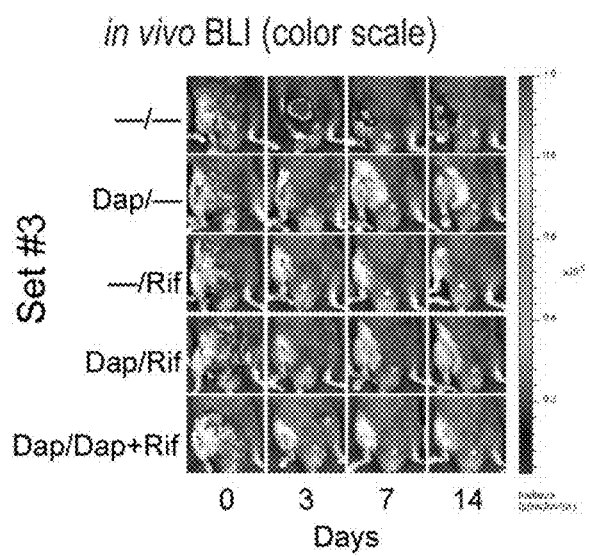
Figure 5I:
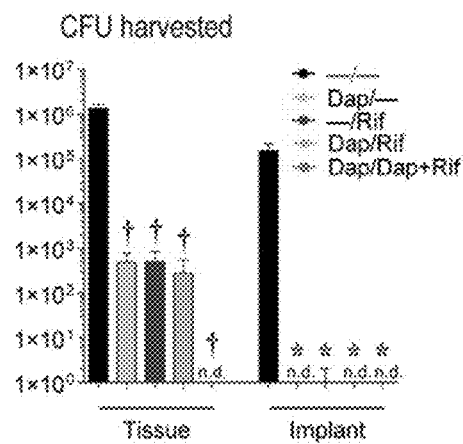
Figure 5J:
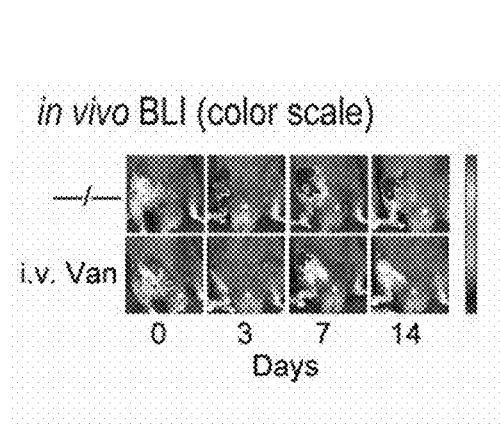
Figure 5K:
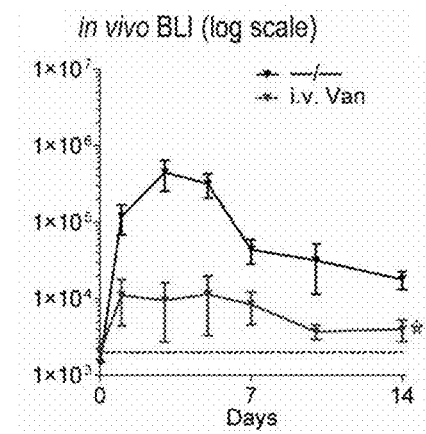
Figure 5L:
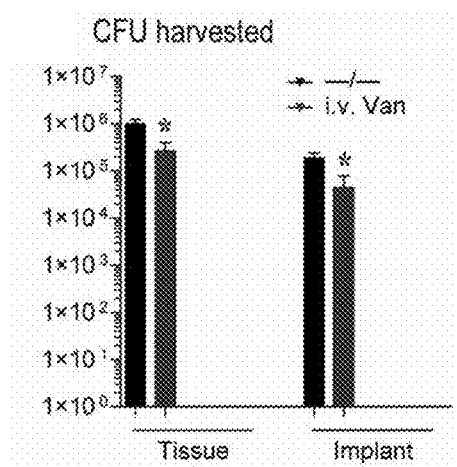

Having thus described the presently disclosed subject matter in general terms, reference will now be made to the accompanying Figures, which are not necessarily drawn to scale, and wherein:

FIG. 1A, FIG. 1B, FIG. 1C, FIG. 1D, and FIG. 1E show a representative PLGA/PCL composite antibiotic-loaded implant coating. FIG. 1A shows a "co-electrospinning" technique in which PLGA and PCL polymers are simultaneously applied onto the metal, e.g., titanium, K-wire implants followed by heat-treatment to generate a conformal PCL film embedded with PLGA fibers. FIG. 1B shows micrograph of uncoated (left), nanofiber-coated after electospinning (center), and annealed (right) composite film-coated K-wire implants. FIG. 1C shows SEM images of composite coated implants with different ratios of PLGA/PCL (w/w). FIG. 1D shows fluorescent micrographs of a composite coating of two electrospun PLGA/PCL layers with the first layer containing FITC-loaded PLGA nanofibers (green) and the second layer containing rhodamine-loaded PLGA nanofibers (red) embedded in PCL film (not visible). FIG. 1E shows a table containing in vitro and in vivo tested sets of antibiotic-loaded implant coatings;

FIG. 2A and FIG. 2B show that the primary parameters for controlling coating thickness and coating mass were collection time (FIG. 2A) and polymer solution flow rate (FIG. 2B). A linear relationship was observed for both parameters with polymer fibers deposited on the implant;

FIG. 3A, FIG. 3B, FIG. 3C, FIG. 3D, FIG. 3E, and FIG. 3F show in vitro release of antibiotics from coating on titanium K-wire implants. FIG. 3A and FIG. 3B show in vitro Van (FIG. 3A) and Rif (FIG. 3B) release from Set #1 PLGA/PCL coating on titanium K-wire implants. FIG. 3C and FIG. 3D show in vitro Lin (FIG. 3C) and Rif (FIG. 3D) release from Set #2 PLGA/PCL coating on titanium K-wire implants. FIG. 3E and FIG. 3F show in vitro Dap (FIG. 3E) and Rif (FIG. 3F) release from Set #3 PLGA/PCL coating on titanium K-wire implants. Horizontal dotted lines=MIC of XEN36 for each antibiotic: Van (0.5 µg/mL), Lin (2 µg/mL), Dap (0.25 µg/mL), and Rif (0.5 µg/mL). *p<0.05, †p<0.01, ‡p<0.001 for combination antibiotic-loaded coatings versus single antibiotic coatings (two-way ANOVA);

FIG. 4A, FIG. 4B, FIG. 4C, FIG. 4D, FIG. 4E, and FIG. 4F show in vitro antimicrobial activity. Zone of inhibition (ZOI) assays were performed on two identically coated K-wire implants placed on bacterial plates that produced a *Staphylococcus aureus* lawn after overnight culture. The diameter (mean mm±SEM) of the ZOI was measured for each of the coatings in Sets #1 (FIG. 4A), #2 (FIG. 4B) and #3 (FIG. 4C). The in vitro antimicrobial activity was also quantified by mixing the antibiotic release solutions from days 1, 3, 7, and 14 with *S. aureus*-containing broth (1×10³ CFU/mL) at a 1:1 (v/v) ratio and comparing CFU after 18 hours of incubation. The antimicrobial activity was quantified for each of the coatings in Sets #1 (FIG. 4D), #2 (FIG. 4E) and #3 (FIG. 4F). *p<0.05, †p<0.01, ‡p<0.001 for combination antibiotic-loaded coatings versus single antibiotic coatings (two-way ANOVA);

FIG. 5A, FIG. 5B, FIG. 5C, FIG. 5D, FIG. 5E, FIG. 5F, FIG. 5G, FIG. 5H, FIG. 5I, FIG. 5J, FIG. 5K and FIG. 5L show in vivo efficacy of vancomycin (Van)/rifampin (Rif) (FIG. 5A, FIG. 5B, and FIG. 5C), linezolid (Lin)/Rif (FIG. 5D, FIG. 5E, and FIG. 5F), daptomycin (Dap)/Rif (FIG. 5G, FIG. 5H, and FIG. 5I) loaded PLGA/PCL coatings on titanium K-wire implants against *S. aureus* in a mouse model of PJI, and intravenous Van prophylaxis (FIG. 5J, FIG. 5K, and FIG. 5L). Horizontal dotted lines=MIC of XEN36 for each antibiotic: Van (0.5 µg/mL), Lin (2 µg/mL), Dap (0.25 µg/mL), and Rif (0.5 µg/mL). *p<0.05, †p<0.01, ‡p<0.001 for antibiotic-loaded coatings versus −/−control coating (two-way ANOVA [in vivo BLI] or two-tailed Student's t-test [CFU]);

FIG. 6A, FIG. 6B, FIG. 6C, and FIG. 6D show SEM images of implants coated with PLGA/PCL composite coating (FIG. 6A), Van-PLGA/Rif-PCL composite coating (FIG. 6B)), Lin-PLGA/Lin+Rif-PCL composite coating (FIG. 6C), and Dap-PLGA/Dap+Rif-PCL composite coating (FIG. 6D). Implants were taken out from the mice infection model after 14 days. Biofilm was observed on the PLGA/PCL coating, while no sign of bacteria or biofilm were found on the remaining three composite coating groups. The larger spherical structures in the areas of the biofilm are adhered bone marrow cells (FIG. 6B and FIG. 6D);

FIG. 7A, FIG. 7B, FIG. 7C, FIG. 7D, FIG. 7E, FIG. 7F, FIG. 7G, FIG. 7H, and FIG. 7I show X-ray analysis of Van/Rif (FIG. 7A, FIG. 7B, and FIG. 7C), Lin/Rif (FIG. 7D, FIG. 7E, and FIG. 7F), or Dap/Rif (FIG. 7G, FIG. 7H, and FIG. 7I) loaded PLGA/PCL coatings on titanium K-wire implants against *S. aureus* in a mouse model of PR In the combined coatings (Van/Rif, Lin/Lin+Rif, and Dap/Dap+Rif), there was decreased femur bone width and femur bone size on day 14 after infection. Data shown revealed significantly improved in vivo bacterial clearance with all combined antibiotic coatings as well as coatings containing Rif alone or Lin alone. *p<0.05, †p<0.01, ‡p<0.001 for antibiotic-loaded coatings versus −/− control coating (one-tailed unpaired Student's t-test).

Figure 8:
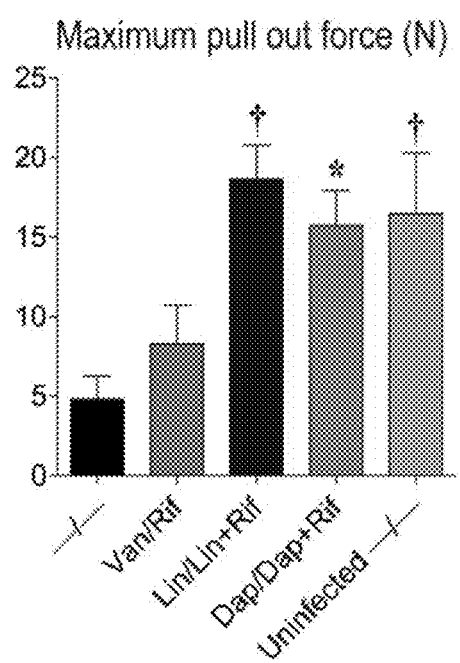
Figure 10:
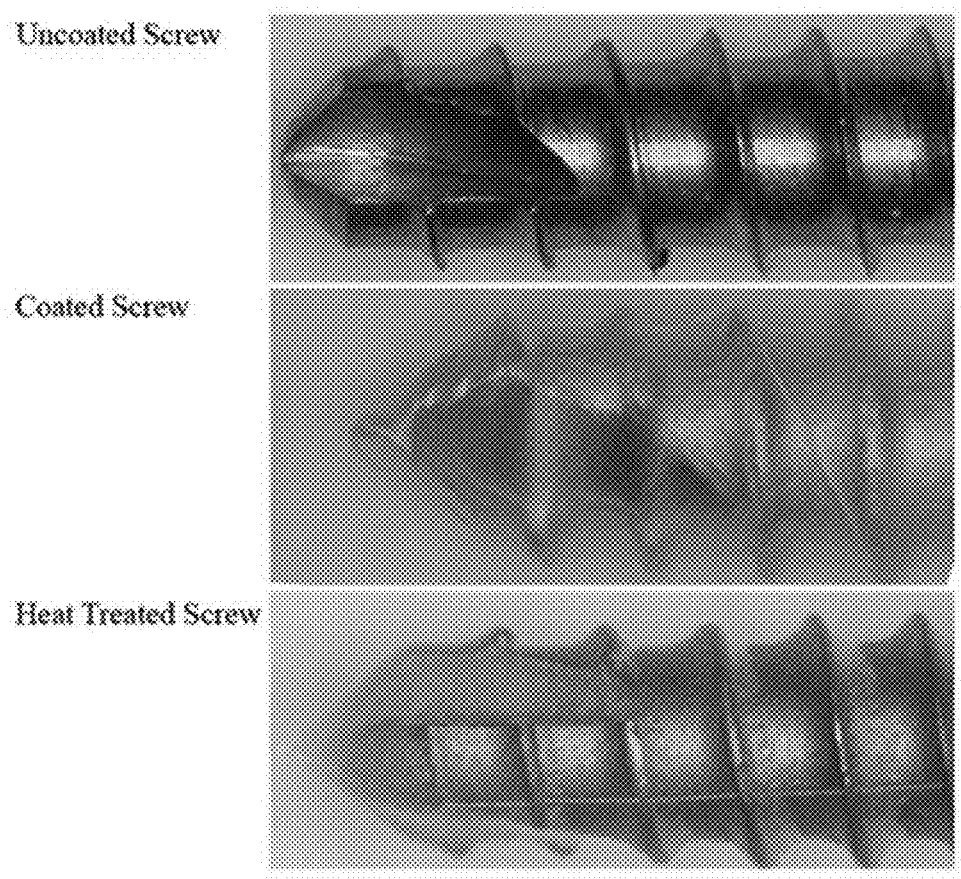
Figure 11A:
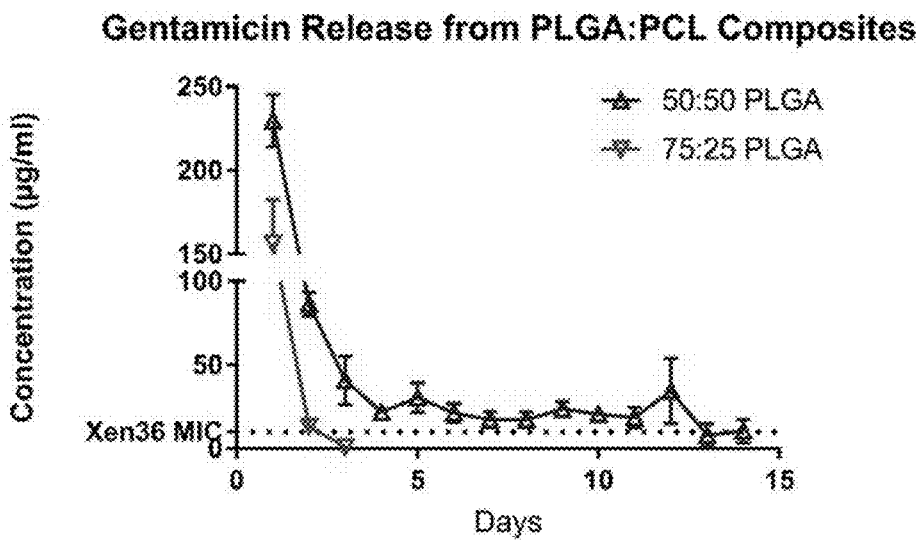
Figure 11B:
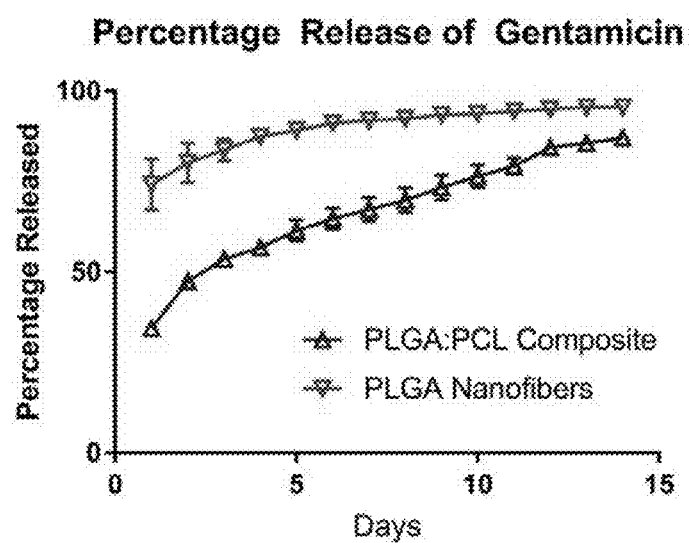
Figure 12A:
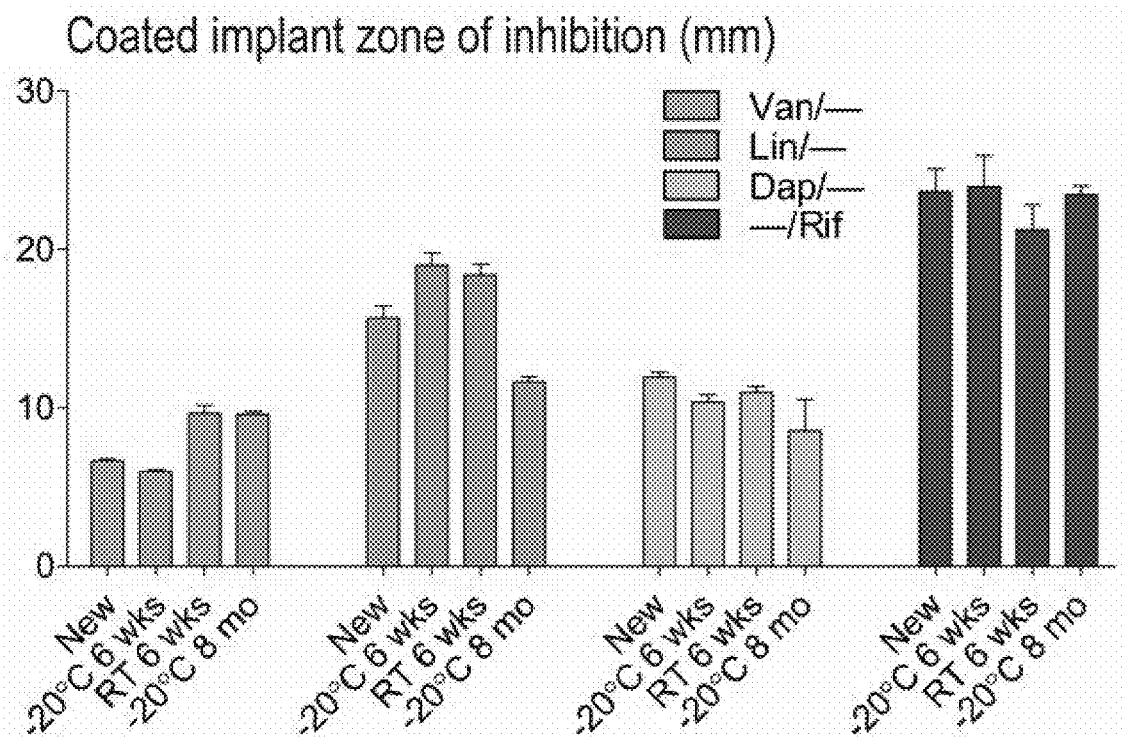
Figure 12B:
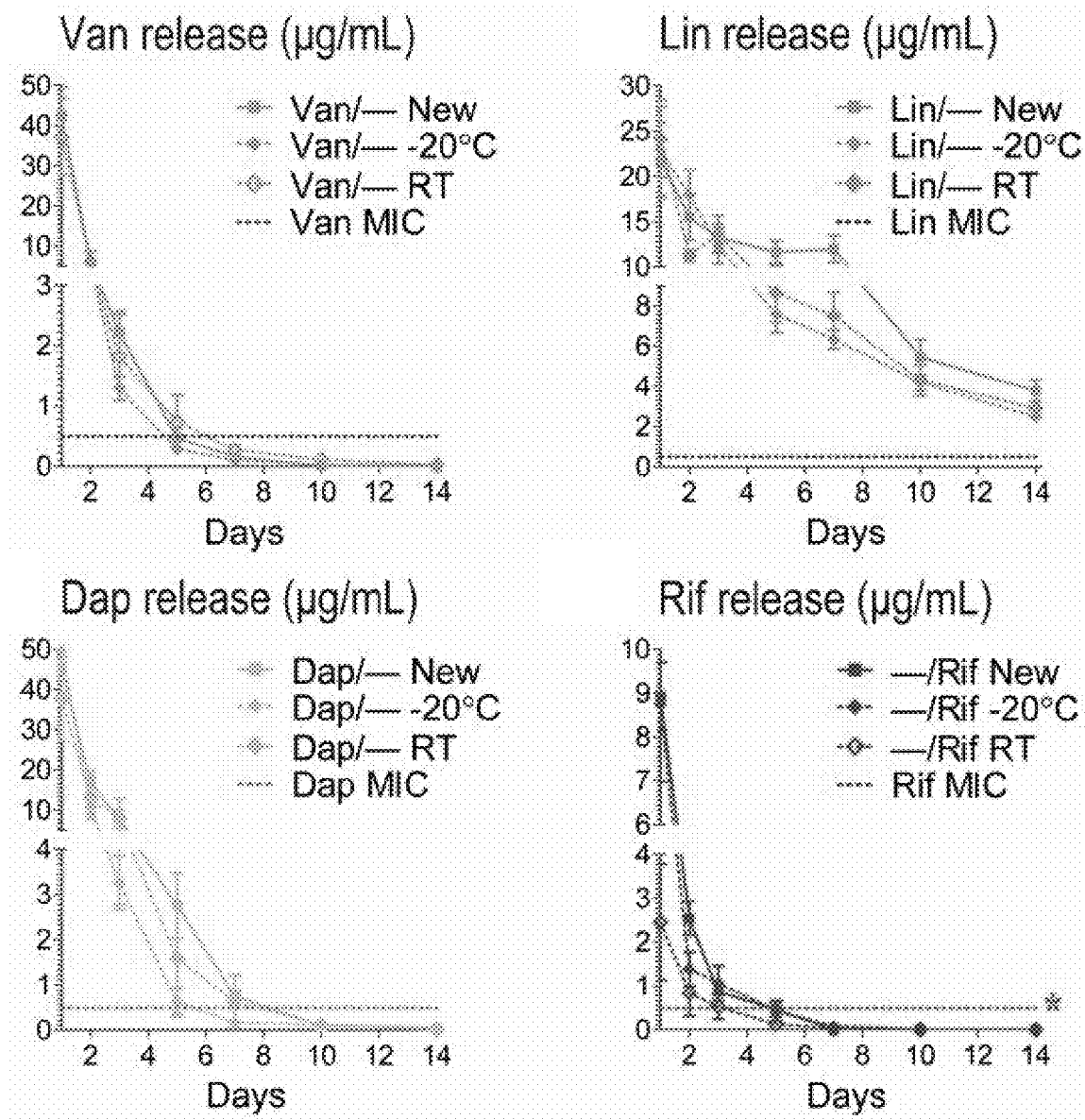
Figure 13A:
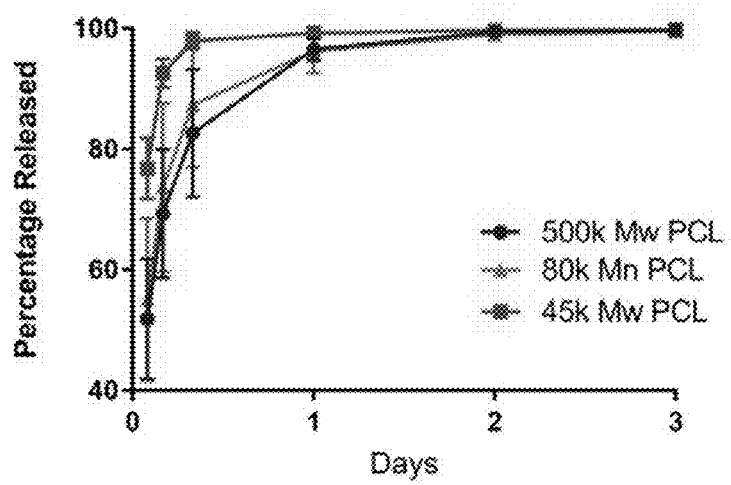
Figure 13B:
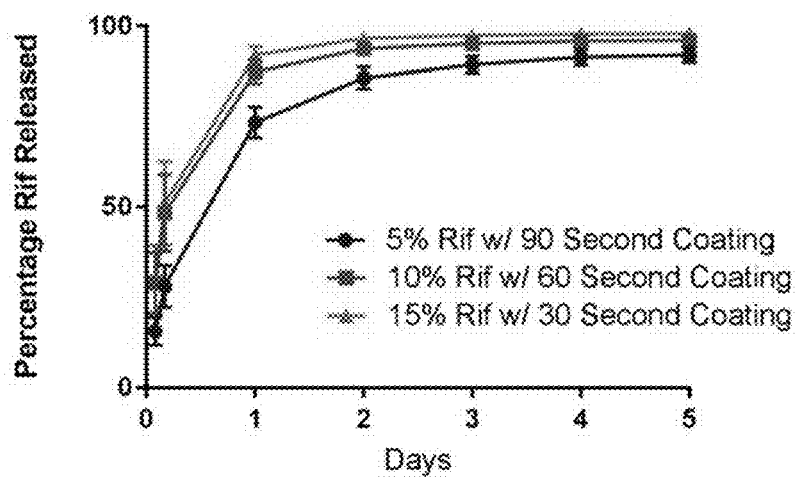
Figure 14A:
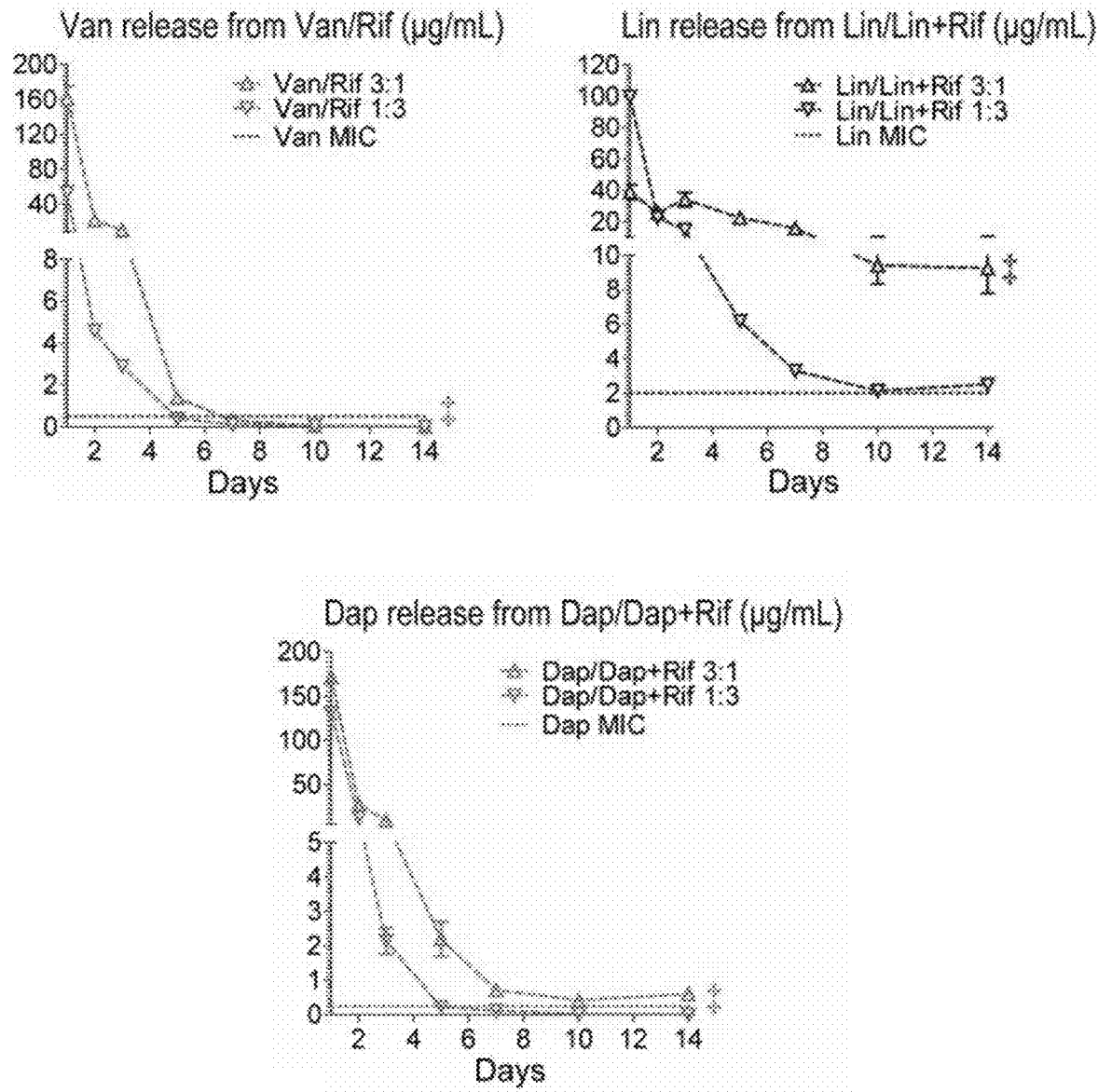
Figure 14B:
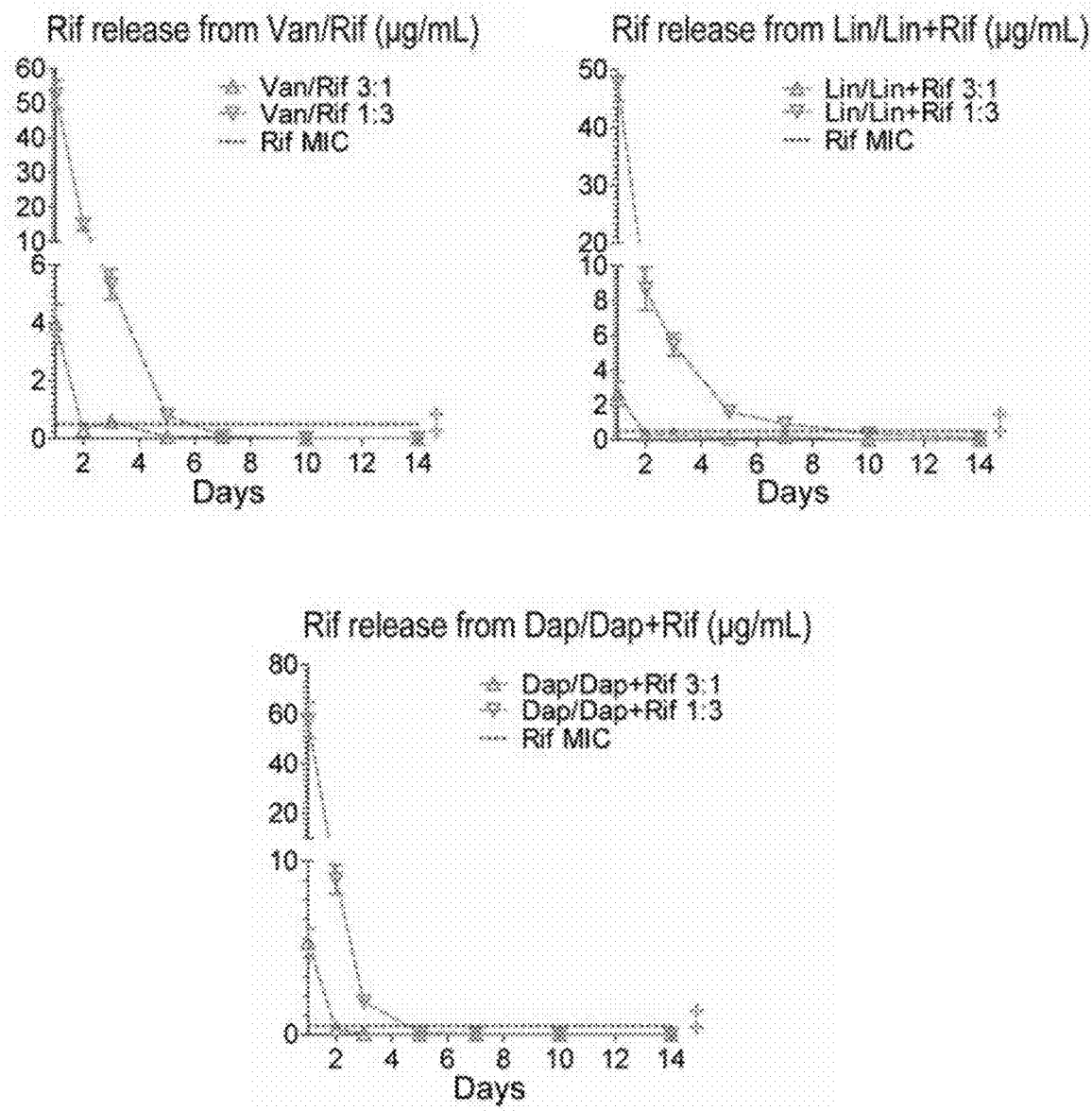

FIG. 8 shows biomechanical pull-out testing to measure the force (mean N SEM) required to pull the coated implants from the bone. *p<0.05, †p<0.01, ‡p<0.001 for antibiotic-loaded coatings versus −/− control coating or −/− coating in uninfected (sterile) mice (two-tailed unpaired Student's t-test);

FIG. 9A and FIG. 9B show in vivo release kinetics as measured by PCL coatings impregnated with a near-infrared (NIR) fluorescent dye Indocyanine green (ICG) as a surrogate for the antibiotic loaded coatings. FIG. 9A shows mean ICG release from coatings measured by in vivo fluorescence imaging (mean total radiant efficiency [photons/s]/[µW/cm²]) over 14 days (left) and the first 24 hours (right). FIG. 9B shows representative in vivo fluorescent signals of the ICG-PCL coatings of the data quantified in FIG. 9A on a color scale overlaid on grayscale images of the mice;

FIG. 10 shows a Biomet Peg screw (SP30000) that has been coated with the composite film coating. Images show the screw prior to electrospinning, after electrospinning and the coated implant after heat treatment;

FIG. 11A and FIG. 11B show the release of Gentamicin from the PLGA nanofibers of the composite polymer coating over the course of 14 days. FIG. 11A shows the in vitro release kinetics from either 50:50 ratio PLGA or 75:25 PLGA with Gentamicin concentrations in μg/mL. FIG. 11B shows the percent of total loaded Gentamicin that was released from either the PLGA nanofiber alone or the PLGA nanofibers when embedded into a PCL film layer;

FIG. 12A and FIG. 12B shows the results of in vitro antimicrobial zone of inhibition studies and in vitro antibiotic release studies for coated pins that were subjected to storage conditions of 6 weeks at room temperature, 6 weeks at −20° C. or 8 months at −20° C. The data shows that the loaded antibiotics in the composite coating retain their antimicrobial efficacy under a variety of storage conditions;

FIG. 13A and FIG. 13B show the percent of loaded Rifampin that is released from the PCL layer of the composite coating when various electrospinning conditions are modified. FIG. 13A shows the effect of modifying PCL molecular weight on the release profiled of Rif. FIG. 13B shows the release rate of Rif from three coatings with different PCL thickness when controlling for overall Rif loading; and FIG. 14A and FIG. 14B shows that modifying the ratio of PLGA nanofiber and PCL film layer can be used to fine tune the antibiotic release from either polymer component. FIG. 14A shows the in vitro release profiles of Van, Lin or Dap loaded into the composite coating. The total antibiotic loading remained constant in the Lin/Lin+Rif and Dap/Dap+Rif ratio groups and varied according to the PLGA ratio for the Van/Rif group. FIG. 14B shows the release profiles of Rif in the same set of pins. Rif loading in the coatings varied in proportion to the PCL ratio of the composite film.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The practice of the presently disclosed subject matter will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science, and Current Protocols in Cell Biology*, all John Wiley & Sons, N.Y., edition as of December 2008; Sambrook, Russell, and Sambrook, *Molecular Cloning. A Laboratory Manual*, 3$^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange 10$^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, available on the World Wide Web: http://www.ncbi.nlm.nih.gov/omim/ and in Online Mendelian Inheritance in Animals (OMIA), a database of genes, inherited disorders and traits in animal species (other than human and mouse), available on the World Wide Web: http://omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

I. Compositions and Methods for Preparation of Composite Polymer Coatings on Medical Implants, and their Use for Co-Delivery of Multiple Antimicrobial Agents Infection is a major complication associated with implantable medical devices and prostheses, resulting in difficult to treat infections. To date, there has been no effective clinical solution that combines antibacterial efficiency with excellent osseointegration. One of the most practical approaches to overcome biofilm-mediated infection involves the use of an antibiotics-loaded, biodegradable polymeric implant coating (Bjarnsholt et al., 2013; Campoccia et al., 2013). Sustained release of antimicrobial agents from the polymeric coating maintains local antibiotic concentration during the entire perioperative period, inhibiting the initial microbial colonization, thereby preventing biofilm formation on implant surfaces. Rifampin is a commonly used antibiotic in the medical treatment of biofilm-associated infections (Lora-Tamayo et al., 2013; Senneville et al., 2011) due to its biofilm-penetrating capability and activity against dormant bacteria (Raad et al., 2007; Saginur et al., 2006). However, it is contraindicated for rifampin to be used as a single agent because of the rapid emergence of resistant bacteria (Osmon et al., 2013). Therefore, rifampin is administered in combination with other active antimicrobial agents, such as vancomycin, linezolid, or daptomycin in the treatment of infections caused by staphylococcal species (Liu et al., 2011), which are frequently associated with the biofilm formation on implants (Darouiche, 2006).

The presently disclosed subject matter provides, in some embodiments, a nanofiber-based conformal coating capable of controlled and independent local delivery of two or more combinatorial antibiotics to provide optimal antimicrobial activity for the prevention of biofilm-associated infections. In a preclinical animal model of orthopaedic implant infection, this presently disclosed method and composition demonstrated complete bacterial clearance from the implant and surrounding bone/joint tissue while promoting osseointegration. This tunable nanofiber composite coating could be highly effective in preventing medical device infections in patients.

More particularly, in some embodiments, the presently disclosed subject matter provides a coating composition which allows for the co-delivery of two or more bioactive agents with independent control of loading level and release profile for each bioactive agent, an implantable medical device coated with the coating composition, and methods of preparing the coating composition. In some embodiments, the coating composition allows for optimization of bioactive agent release kinetics to maximize antimicrobial activity against biofilm formation in vivo.

Combination therapy using at least two bioactive agents has the potential not only to prevent the development of antibiotic resistance, but also to achieve synergistic antimicrobial activity. Since each procedure is dependent on particular clinical conditions, the duration, ratio of the bioactive agents applied, and loading level and release profile of each bioactive agent can be independently tunable to afford maximum flexibility for dosing selection.

A. Coating Composition

In some embodiments, the presently disclosed subject matter provides a coating composition comprising: (a) a polymer film produced from a first set of polymer nanofibers with a first capacity for loading of at least a first bioactive agent that is released in vivo at a first release rate; (b) at least a second set of polymer nanofibers embedded in the polymer film, wherein the second set of polymer nanofibers comprise at least a second capacity for loading of at least one of the first bioactive agent or at least a second bioactive agent that is released in vivo at a second release rate, wherein the first capacity for loading of the first bioactive agent in the polymer film is independent of the second capacity for loading of the at least one of the first bioactive agent or second bioactive agent, and wherein the first release rate of the first bioactive agent in vivo from the polymer film is independent of the second release rate of the at least one of the first bioactive agent or second bioactive agent in vivo from the at least second set of polymer nanofibers; and (c) at least one of the first bioactive agent or second bioactive agent loaded in the polymer film and/or in the second set of polymer nanofibers.

As used herein, the term "coating" refers to a layer of a substance, e.g., a layer of a polymeric substance. In some embodiments, the polymer film in the coating composition is produced from the first set of polymer nanofibers using the presently disclosed methods comprising electrospinning, annealing, and cooling under controlled parameters.

In some embodiments, the polymer film is loaded with the first bioactive agent. In some embodiments, the second set of polymer nanofibers is loaded with the first bioactive agent. In some embodiments, the polymer film and the second set of polymer nanofibers are each loaded with either the first bioactive agent or the second bioactive agent. In some embodiments, the coating composition further comprises at least a third set of polymer nanofibers, wherein the polymer film is loaded with the first bioactive agent, the second set of polymer nanofibers is loaded with the second bioactive agent, and the third set of polymer nanofibers is loaded with at least a third bioactive agent. In some embodiments, the first bioactive agent, the second bioactive agent, and the third bioactive agent are each different bioactive agents. In some embodiments, because each bioactive agent is partitioned into a different set of polymer nanofibers and/or polymer film, the release of each bioactive agent can be tuned separately.

In some embodiments, only one bioactive agent is loaded into the polymer film and/or into a set of polymer nanofibers. In some embodiments, more than one bioactive agent is loaded into the polymer film and/or into a set of polymer nanofibers, such as 2, 3, 4, 5, 6 or more bioactive agents. In some embodiments, more than one bioactive agent is loaded into the polymer film and/or into a set of polymer nanofibers at the same time. In some embodiments, more than one bioactive agent is loaded into the polymer film and/or into a set of polymer nanofibers at different times.

In some embodiments, the first set of polymer nanofibers, the second set of polymer nanofibers, and the third set of polymer nanofibers each comprise a different homopolymer or copolymer. In some embodiments, the first set of polymer nanofibers, the second set of polymer nanofibers, and the third set of polymer nanofibers each comprise a homopolymer or copolymer of monomers selected from the group consisting of ε-caprolactone, D-lactide, L-lactide, and glycolide. In some embodiments, the second set of polymer nanofibers and/or the third set of polymer nanofibers comprise poly(D,L-lactide-co-glycolide).

In some embodiments, the first set of polymer nanofibers comprises a polymer that is selected from the group consisting of poly(ε-caprolactone), a copolymer of ε-caprolactone and D-lactide, a copolymer of ε-caprolactone and L-lactide, and a copolymer of ε-caprolactone and glycolide. In some embodiments, the first set of polymer nanofibers comprises poly(ε-caprolactone). In some embodiments, the first set of polymer nanofibers comprises a copolymer of ε-caprolactone and D-lactide. In some embodiments, the first set of polymer nanofibers comprises a copolymer of ε-caprolactone and L-lactide. In some embodiments, the first set of polymer nanofibers comprises a copolymer of ε-caprolactone and glycolide. In some embodiments, the first set of polymer nanofibers comprises poly(ε-caprolactone), and the second set of polymer nanofibers and/or the third set of polymer nanofibers comprise poly(D,L-lactide-co-glycolide).

As used herein, the term "homopolymer" refers to a polymer that comprises only one type of monomer and the term "copolymer" refers to a polymer comprising at least two types of monomers. In some embodiments, the set of polymer nanofibers is a polymer blend. In some embodiments, the type of polymer and/or polymer blends is chosen to adjust the degradation rate of the coating and/or adjust the release rate of a bioactive agent.

In some embodiments, the weight ratio of the at least second set of polymer nanofibers and the polymer film is from about 80:20 to about 10:90. In some embodiments, the weight ratio of poly(D,L-lactide-co-glycolide) to poly(ε-caprolactone) is from about 80:20 to about 10:90. In some embodiments, the polymer nanofibers have an average diameter from about 50 nm to about 10 μm. In some embodiments, the polymer film has an average thickness from about 20 μm to about 500 μm.

In some embodiments, the coating composition is prepared from biodegradable polymers. As used herein, "biodegradable" polymers are those that, when introduced into cells, are broken down by the cellular machinery or by hydrolysis into components that the cells can either reuse or dispose of without significant toxic effect on the cells (i.e., fewer than about 20% of the cells are killed when the polymers are added to cells in vitro). The polymers preferably do not induce inflammation or other adverse effects in vivo.

Generally, to be biodegradable, the presently disclosed polymers contain a degradable linkage. Representative degradable linkages include, but are not limited to:

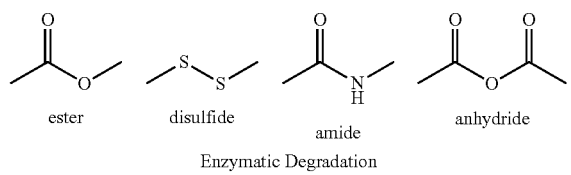

Enzymatic Degradation

Depending on the ratio of the polymer nanofibers and the polymer film, in some embodiments, the polymer film resulting from the presently disclosed methods is smooth and in other embodiments, the polymer film is rough with nanofibers exposed on the surface to different degrees. Generally, it has been found that a higher ratio of the polymer nanofibers to the polymer film results in a rougher surface.

In some embodiments, the bioactive agent is selected from the group consisting of small molecules, such as small organic or inorganic molecules; saccharides; oligosaccharides; polysaccharides; a biological macromolecule selected from the group consisting of peptides, proteins, peptide analogs and derivatives; peptidomimetics; nucleic acids, such as DNA, RNA interference molecules, selected from the group consisting of siRNAs, shRNAs, antisense RNAs, miRNAs and ribozymes, dendrimers and aptamers; antibodies, including antibody fragments and intrabodies; an extract made from biological materials selected from the group consisting of bacteria, plants, fungi, animal cells, and animal tissues; naturally occurring or synthetic compositions; and any combination thereof.

In some embodiments, the first bioactive agent, the second bioactive agent, and/or the third bioactive agent are selected from the group consisting of a polypeptide, growth factor, a steroid agent, a therapeutic antibody, an antibody fragment, a DNA, an RNA, and siRNA, an antimicrobial agent, an antibiotic, an anti-retroviral agent, an anti-inflammatory agent, an anti-tumor agent, anti-angiogenic agent, and a chemotherapeutic agent. The biological agents may be in a purified form, partially purified form, recombinant form, or any other form appropriate for inclusion in the coating composition.

The term "polypeptide" as used herein refers to a polymer of amino acids. The terms "protein" and "polypeptide" are used interchangeably herein.

As used herein, a "nucleic acid" or "polynucleotide" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

An "RNA interfering agent" as used herein is defined as any agent that interferes with or inhibits expression of a target gene, e.g., by RNA interference (RNAi). Such RNA interfering agents include, but are not limited to, antisense molecules, ribozymes, small inhibitory nucleic acid sequences, for example but not limited to guide RNAs, small interfering RNA (siRNA), short hairpin RNA or small hairpin RNA (shRNA), microRNA (miRNA), post-transcriptional gene silencing RNA (ptgsRNA), short interfering oligonucleotides, antisense oligonucleotides, aptamers, CRISPR RNAs, nucleic acid molecules including RNA molecules which are homologous to the target gene, or a fragment thereof, and any molecule which interferes with or inhibits expression of a target gene by RNA interference (RNAi).

As used herein, the term "antibody" refers to a polypeptide or group of polypeptides which comprise at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', F(ab)$_2$, and F(ab')2 fragments. As used herein, a "therapeutic antibody" is an antibody that recognizes and binds to a cell surface antigen to trigger a biological response. The therapeutic antibody may activate cell membrane receptors to change the cell's functions, block the growth of a tumor, recruit the body's immune system to attack the cell, or sensitize a cancer cell to chemotherapy, for example. The therapeutic antibody may itself be the drug or may be a carrier to target a drug to a specific cell.

In some embodiments, the bioactive agent may be a growth factor that encourages bone or tissue growth. Non-limiting examples of growth factors include platelet derived growth factor (PDGF), transforming growth factor β (TGF-β), insulin-related growth factor-I (IGF-I), insulin-related growth factor-II (IGF-II), fibroblast growth factor (FGF), beta-2-microglobulin (BDGF II), and bone morphogenetic factors. Bone morphogenetic factors are growth factors whose activity is specific to bone tissue including, but not limited to, proteins of demineralized bone, demineralized bone matrix (DBM), and in particular bone protein (BP) or bone morphogenetic protein (BMP). In some embodiments, osteoinductive factors such as fibronectin (FN), osteonectin (ON), endothelial cell growth factor (ECGF), cementum attachment extracts (CAE), ketanserin, human growth hormone (HGH), animal growth hormones, epidermal growth factor (EGF), interleukin-1 (IL-1), human alpha thrombin, transforming growth factor (TGF-beta), insulin-like growth factor (IGF-1), platelet derived growth factors (PDGF), and fibroblast growth factors (FGF, bFGF, etc.) also may be considered a bioactive agent.

As used herein, the term "antiretroviral drug" refers to a drug that is used for the treatment of infection by a retrovirus. Non-limiting examples of antiretroviral drugs include nucleoside and nucleotide reverse transcriptase inhibitors, non-nucleoside reverse transcriptase inhibitors, protease inhibitors, and integrase inhibitors.

As used herein, the term "anti-inflammatory compound" refers to a compound that may be used to prevent or reduce an inflammatory response or inflammation in a cell, tissue, organ, or subject. In some embodiments, anti-inflammatory agents include clobetasol, alclofenac, alclometasonedipropionate, algestoneacetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixinmeglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen picobol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednoletabonate, meclofenamate sodium, meclofenamic acid, meclorisonedibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosanpolysulfate sodium, phenbutazone sodium glycerate, pirfenidone, piroxicam, piroxicamcinnamate, piroxicamolamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortolpivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecrolimus, prodrugs thereof, co-drugs thereof, and combinations thereof. The anti-inflammatory agent may also be a biological inhibitor of proinflammatory signaling molecules including antibodies to such biological inflammatory signaling molecules.

As used herein, the term "steroid agent" refers to a compound that is a steroid, such as dexamethasone, hydrocortisone, prednisolone, and triamcinolone, for example.

As used herein, the term "anti-tumor agent" refers to an agent that is capable of inhibiting a tumor, such as anti-angiogenic agents, DNA intercalators or cross-linkers (e.g., doxorubicin and cisplatin), DNA synthesis inhibitors (e.g., methotrexate, hydroxyurea, 5-fluorouracil, and gemcitabine), DNA-RNA transcription regulators, enzyme inhibitors, agents that affect gene regulation, and microtubule inhibitors (e.g., paclitaxel).

As used herein, the term "anti-angiogenic agent" includes but is not limited to bevacizumab, itraconazole, carboxyamidotriazole, TNP-470, CM101, IFN-α, IL-12, platelet factor-4, suramin, SU5416, thrombospondin, VEGFR antagonists, cartilage-derived angiogenesis inhibitory factor, matrix metalloproteinase inhibitors, angiostatin, endostatin, 2-methoxyestradiol, tecogalan, tetrathiomolybdate, thalidomide and thalidomide analogs, thrombospondin, prolactin, αVβ3 inhibitors, COX-2 inhibitors, integrin antagonists, linomide, tasquinimod, ranibizumab, sorafenib, sunitinib, pazopanib, everolimus, vitaxin, celecoxib, rofecoxib, JTE-522, EMD-121974, D-2163, FGFR kinase inhibitors, EGFR kinase inhibitors, marmiastat, prinomastat, BMS275291, BAY12-9566, neovastat, rhuMAb VEGF, SU5416, SU6668, ZD6474, CP-547, CP-632, ZD4190, squalamine, and ZD6126.

As used herein, a "chemotherapeutic agent" is used to connote a compound or composition that is administered in the treatment of cancer. Chemotherapeutic agents include, but are not limited to, alkylating agents, such as thiotepa and cyclophosphamide; alkyl sulfonates, such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas, such as carmustine, chlorozotocin, fotemustine, lomustine, nimustine, ranimustine; antibiotics, such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs, such as ancitabine, azacitidine, 6-azauridine, carmofur, cytosine arabinoside, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenishers, such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g., paclitaxel and docetaxel; chlorambucil; gemcitabine; 6-thioguanine; mercaptopurine; platinum analogs, such as cisplatin and carboplatin; vinblastine; platinum; etoposide; ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine; retinoic acid; esperamicins; capecitabine; and pharmaceutically acceptable salts, acids or derivatives of any of the above.

Chemotherapeutic agents also include anti-hormonal agents that act to regulate or inhibit hormone action on tumors, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, and goserelin; and pharmaceutically acceptable salts, acids or derivatives of any of the above.

In some embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide, and irinotecan, as well as pharmaceutically acceptable salts, acids, or derivatives of any of these.

In some embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain alternative embodiments, the antimitotic agent comprises a *vinca* alkaloid, such as vincristine, vinblastine, vinorelbine, or vindesine, or pharmaceutically acceptable salts, acids, or derivatives thereof.

As used herein, the term "antibiotic" includes without limitation those antibiotics that affect the bacterial cell wall, such as penicillins and cephalosporins, the cell membrane, such as polymyxins, interfere with essential bacterial enzymes, such as rifamycins (e.g., rifampin), lipiarmycins, quinolones, and sulfonamides, target protein synthesis, such as macrolides, lincosamides and tetracyclines, cyclic lipopeptides, such as daptomycin, glycylcyclines, such as tigecycline, oxazolidinones, such as linezolid, lipiarmycins, such as fidaxomicin, fluoroquinolones, such as gemifloxacin, lipoglycopeptides, such as telavancin, and macrocyclics, such as fidaxomicin. In particular, the term "antibiotic" includes, without being limited to, rifampicin, pyrazinamide, ethambutol, streptomycin, isoniazid, amoxicillin, ampicillin, bacampicillin, carbenicillin, cloxacillin, dicloxacillin, flucloxacillin, mezlocillin, nafcillin, oxacillin, penicillin G, penicillin V, piperacillin, pivampicillin, pivmecillinam, ticarcillin, cefacetrile (cephacetrile), cefadroxil (cefadroxyl), cefalexin (cephalexin), cefaloglycin (cephaloglycin), cefalonium (cephalonium), cefaclor, cefamandole, cefmetazole, cefcapene, cefdaloxime, ceftaroline, aztreonam, imipenem, doripenem, meropenem, ertapenem, azithromycin, erythromycin, clarithromycin, dirithromycin, roxithromycin, ketolides, telithromycin, clindamycin, lincomycin, pristinamycin, amikacin, gentamicin, kanamycin, neomycin, flumequine, nalidixic acid, oxolinic acid, piromidic acid, ciprofloxacin, enoxacin, lomefloxacin, balofloxacin, gatifloxacin, grepafloxacin, levofloxacin, sulfamethizole, sulfamethoxazole, sulfisoxazole, demeclocycline, doxycycline, minocycline, oxytetracycline, tetracycline, chloramphenicol, metronidazole, tinidazole, nitrofurantoin, vancomycin, telavancin, linezolid, bacitracin, polymyxin B, and viomycin. In some embodiments, the first bioactive agent, the second bioactive agent, and/or the third bioactive agent are an antibiotic.

In some embodiments, the antibiotic is selected from the group consisting of rifampin, linezolid, vancomycin and daptomycin. In some embodiments, the coating composition comprises: (a) linezolid loaded in the second set of polymer nanofibers, and linezolid and rifampin loaded in the polymer film; or (b) daptomycin loaded in the second set of polymer nanofibers, and daptomycin and rifampin loaded in the polymer film; or (c) vancomycin loaded in the second set of polymer nanofibers and rifampin loaded in the polymer film.

As used herein, the term "release rate" refers to the rate at which a substance, such as a bioactive agent, is released from a coating composition. At least one advantage of the presently disclosed subject matter is that the release rate of each bioactive agent used in the coating composition is independent of any other release rate. As such, the release rates of each bioactive agent can be tuned and multiple bioactive agents can be released simultaneously with multiple release rates. In some embodiments, and without wishing to be bound to any one particular theory, it is believed that the primary mechanism of release of a bioactive agent is by diffusion. In some embodiments, degradation of the polymer nanofibers can be modified as well to tune the release of a bioactive agent. The release rate of a particular bioactive agent can be controlled by the choice of polymer solution, bioactive agent concentration, the type of bioactive agent, and implant surface morphology through polymer formulation and nanofiber structure, for example.

In some embodiments, the coating composition releases the first bioactive agent and the second bioactive agent simultaneously and in a controlled manner, wherein the first bioactive agent is released from the polymer film and the second bioactive agent is released from the second set of polymer nanofibers. As used herein, the term "in a controlled manner" means that the release of a bioactive agent occurs over a period of time. In some embodiments, the release of a bioactive agent occurs at a steady rate.

In some embodiments, the coating composition releases the first bioactive agent and the second bioactive agent simultaneously and immediately in a controlled manner, wherein the first bioactive agent is released from the polymer film and the second bioactive agent is released from the second set of polymer nanofibers. As used herein, the term "immediately" refers to the start of the release of a bioactive agent as soon as the coating composition is put into use, such as when a medical device coated with the coating composition is implanted in a patient. In some embodiments, the bioactive agent is released immediately but sustained over a period of time.

In some embodiments, the coating composition releases the first bioactive agent and the second bioactive agents simultaneously and immediately at different release rates in a controlled manner. In some embodiments, the coating composition releases the first bioactive agent and the second bioactive agent simultaneously and immediately at different release rates in a controlled manner, wherein the first bioactive agent is released from the polymer film and the second bioactive agent is released from the second set of polymer nanofibers.

In some embodiments, a bioactive agent is released from the coating composition over a time period of several days to several weeks. In some embodiments, a bioactive agent is released from the coating composition over a time period ranging from about 2 days to about 6 months. In some embodiments, a bioactive agent is released from the coating composition over about 2 days, about 3 days, about 7 days, about 2 weeks, about 3 weeks, about 4 weeks, about 6 weeks, about 8 weeks, about 12 weeks, or more. In some embodiments, the coating composition releases the first bioactive agent, the second bioactive agent, and/or the third bioactive agent over a time period of about three days to about four weeks.

B. Implantable Medical Device Comprising a Conformal Coating

In some embodiments, the presently disclosed subject matter provides an implantable medical device comprising: (a) a metallic surface; and (b) a conformal coating on at least a portion of the metallic surface, the conformal coating comprising: (i) a polymer film produced from a first set of polymer nanofibers with a first capacity for loading of at least a first bioactive agent that is released in vivo at a first release rate; (ii) at least a second set of polymer nanofibers embedded in the polymer film, wherein the second set of polymer nanofibers comprise at least a second capacity for loading of at least one of the first bioactive agent or at least a second bioactive agent that is released in vivo at a second release rate, wherein the first capacity for loading of the first bioactive agent in the polymer film is independent of the second capacity for loading of the at least one of the first bioactive agent or second bioactive agent, and wherein the first release rate of the first bioactive agent in vivo from the polymer film is independent of the second release rate of the at least one of the first bioactive agent or second bioactive agent in vivo from the at least a second set of polymer nanofibers; and (iii) at least one of the first bioactive agent or second bioactive agent loaded in the polymer film and/or in the second set of polymer nanofibers.

As used herein, the term "implantable medical device" is a medical device that is capable of being introduced into a patient, such as by surgical or other medical means, and is intended to remain in the patient after the procedure. As used herein, the term "metallic surface" refers to the surface, such as of a medical device that comprises a metal or a metallic alloy, such as iron, cobalt, chromium, titanium, aluminum, nickel, and tantalum, for example.

As used herein, the term "conformal coating" refers to a coating that conforms to the contours of the surface that it is on. In some embodiments, the conformal coating further comprises advantageous biological agents and additives to impart, for example, additional osteoinductive and osteoconductive properties to the implantable medical device. In some embodiments, the coating composition, such as the polymer film, further comprises hydroxyapatite nanocrystals to impart osseointegration properties to the implantable medical device.

In some embodiments, the implantable medical device is an orthopedic device, a dental device, a cardiovascular device, a neurological device, a neurovascular device, a gastrointestinal device, a muscular device, an intramedullary device, or an ocular device. In some embodiments, the implantable medical device is an artificial joint, such as an artificial hip or knee, an internal fracture-fixation device, an external fracture-fixation device, a device for fixation of small bones, a device for fixation of the spine, a pacemaker, an implantable cardioverter-defibrillator, a stent, a nail (e.g., a Talwalker nail, a Rush nail), a rod (e.g., a Luque rod), a screw, a plate, a clip, or a pin (e.g., a Steinmann pin).

In some embodiments, the presently disclosed coating minimizes infections, such as post-surgical infections. In some embodiments, the conformal coating inhibits at least one genus of bacteria, such as those bacteria that enter into a patient because of a surgery. In some embodiments, the genus of bacteria is selected from the group consisting of *Staphylococcus, Acinetobacter, Klebsiella, Enterococcus, Streptococcus, Escherichia, Proteus, Pseudomonas, Propionibacterium* and *Vibrio*.

In some embodiments, the presently disclosed subject matter provides a method for reducing or preventing the formation of a biofilm in vivo after implantation of an implantable medical device into a patient, the method comprising implanting an implantable medical device comprising a metallic surface into a patient, wherein at least a portion of the metallic surface is coated with a conformal coating comprising: (a) a polymer film produced from a first set of polymer nanofibers; (b) at least a second set of polymer nanofibers; and (c) at least two different antibiotic agents loaded into the polymer film and/or the at least second set of polymer nanofibers; wherein upon implantation of the implantable medical device into the patient, the at least two different antibiotic agents are simultaneously and immediately released at different, independent release profiles, thereby reducing or preventing the formation of the biofilm in vivo.

C. Method for Coating an Implantable Medical Device

In some embodiments, the presently disclosed subject matter provides a method for coating an implantable medical device with a conformal coating comprising at least a first bioactive agent, the method comprising: (a) depositing onto at least a portion of a metallic surface of an implantable medical device using electrospinning: (i) a plurality of polymer nanofibers, wherein the plurality of polymer nanofibers comprise at least a first set of polymer nanofibers with a melting temperature of about 40° C. to about 100° C. and at least a second set of polymer nanofibers with a higher melting temperature than the melting temperature of the first set of polymer nanofibers; and (ii) at least a first bioactive agent loaded into the first set of polymer nanofibers and/or the second set of polymer nanofibers; and (b) annealing the implantable medical device for a controlled time period at a controlled temperature that is higher than the melting temperature of the first set of polymer nanofibers; thereby coating the implantable medical device with the conformal coating comprising the first bioactive agent. In some embodiments, the presently disclosed methods further comprise cooling the implantable device to form a solid coating comprising the plurality of polymer nanofibers and the first bioactive agent.

In some embodiments, the presently disclosed subject matter provides a method for coating an implantable medical device with a conformal coating comprising at least a first bioactive agent, the method comprising: (a) depositing onto at least a portion of a metallic surface of an implantable medical device using electrospinning: (i) a plurality of polymer nanofibers, wherein the plurality of polymer nanofibers comprise at least a first set of polymer nanofibers with a melting temperature of about 40° C. to about 100° C. and at least a second set of polymer nanofibers with a higher melting temperature than the melting temperature of the first set of polymer nanofibers; and (ii) at least a first bioactive agent loaded into the first set of polymer nanofibers and/or the second set of polymer nanofibers; (b) annealing the implantable medical device for a controlled time period at a controlled temperature that is higher than the melting temperature of the first set of polymer nanofibers; and (c) cooling the implantable device to form a solid coating comprising the plurality of polymer nanofibers and the first bioactive agent; thereby coating the implantable medical device with the conformal coating comprising the first bioactive agent.

In step (a) of the presently disclosed method, electrospinning is used to deposit the plurality of polymer nanofibers and at least one bioactive agent onto at least a portion of a metallic surface of an implantable device. As used herein, the term "electrospinning" refers to a method which uses a co-spinning process with at least two injection streams of polymer solution to create a mixed nano-fibrous matrix of the polymers.

As used herein, the term "plurality of polymer nanofibers" refers to at least two sets of polymer nanofibers, of which at least one set of polymer nanofibers has a melting temperature that is higher than the melting temperature of at least another set of polymer nanofibers. Because of the different melting temperatures of the sets of polymer nanofibers, at least one set of polymer nanofibers in the plurality of polymer nanofibers can be melted to form a polymer film, while at least another set of polymer nanofibers does not melt, thereby forming at least one set of polymer nanofibers embedded in a polymer film. In some embodiments, the number of sets of polymer nanofibers in the plurality of polymer nanofibers is two. In some embodiments, the number of sets of polymer nanofibers in the plurality of polymer nanofibers is three.

In step (b) of the presently disclosed method, the implantable medical device is annealed for a controlled time period at a controlled temperature. As used herein, the term "annealing" refers to treating a material with heat. In some embodiments, annealing the implantable medical device occurs at a controlled temperature that is from about 10° C. to about 20° C. higher than the melting temperature of the first set of polymer nanofibers. In some embodiments, annealing occurs at a controlled temperature that is from about 50° C. to about 80° C. In some embodiments, annealing occurs at a controlled temperature that is from about 60° C. to about 75° C. In some embodiments, annealing occurs at a controlled temperature that is from about 65° C. to about 75° C. In some embodiments, the term "controlled temperature" may mean that the implantable medical device is not heated at one specific temperature, but is heated at more than one temperature. For example, the implantable medical device may be heated starting at 50° C. and then the temperature may be increased, such as to 70° C.

In some embodiments, the controlled temperature does not significantly reduce the bioactivity of the first bioactive agent and/or the second bioactive agent. As used herein, the term "significantly reduce" means a decrease in a parameter, such as the bioactivity of a bioactive agent, as detected by methods known in the art. As used herein, "significantly reduce" includes a 10% change, preferably a 25% change, more preferably a 40% change, and even more preferably a 50% or greater change.

In some embodiments, the controlled time period for annealing is from about 10 seconds to about 20 minutes, such as from about 1 minute to about 15 minutes, about 1 minute to about 5 minutes, from about 5 minutes to about 10 minutes, and from about 10 minutes to about 15 minutes.

In some embodiments, step (a) and/or steps (a) and (b) are repeated at least one time to generate a layered coating on the implantable medical device. In some embodiments, step (a) is repeated to deposit at least a third set of polymer nanofibers and either the first bioactive agent and/or at least a second bioactive agent onto at least a portion of the metallic surface of the implantable medical device.

In step (c) of the presently disclosed method, the implantable medical device is cooled. In some embodiments, cooling is performed actively by moving the implantable medical device into a cool environment, such as a refrigerator. In some embodiments, cooling is performed passively, by allowing the implantable medical device to cool at room temperature, for example. In some embodiments, steps (b) and (c) result in a solid, conformal coating forming on the implantable medical device.

In some embodiments, the loading level, measured by weight percentage of the incorporated bioactive agent among the total weight of nanofibers, of at least one of the first bioactive agent or second bioactive agent in the first set of polymer nanofibers and/or second set of polymer nanofibers is from about 1% to about 50%, such as from about 5% to about 50%, from about 10% to about 40%, or from about 20% to about 40%.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

The terms "subject" and "patient" are used interchangeably herein. The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Composite Fiber-Film Coating

Bacterial biofilm formation is a major complication of implantable medical devices that results in therapeutically challenging chronic infections, especially in cases involving antibiotic-resistant bacteria. As an approach to prevent these infections, an electrospun composite coating comprised of poly(lactic-co-glycolic acid) nanofibers embedded in a poly (ε-caprolactone) film was developed to locally co-deliver combinatorial antibiotics from the implant surface. The release of each antibiotic could be adjusted by loading each drug into the different polymers or by varying PLGA:PCL polymer ratios. In a mouse model of biofilm-associated orthopaedic-implant infection, three different combinations of antibiotic-loaded coatings were highly effective in preventing infection of the bone/joint tissue and implant biofilm formation and were biocompatible with enhanced osseointegration. This nanofiber composite coating technology could be used to tailor the delivery of combinatorial antimicrobial agents from various metallic implantable devices or prostheses to effectively decrease biofilm-associated infections in patients.

Materials and Methods

FIG. 1A illustrates a representative method for coating a metallic surface with a presently disclosed coating composition. PLGA (75:25, MW 66,000-107,000, Sigma, St. Louis, Mo., USA) solution (10.0 w/w %) in hexafluoro-2-propanol (HFIP) was loaded in a 1-mL syringe fitted with a 27-gauge blunt-end needle. A polymer solution was fed into the needle tip at a flow rate of 0.5 mL/h, controlled using a syringe pump. High-voltage power supplies were connected to the needles through alligator clips and a voltage differential of 7 kV was applied between the needle and the collector plate. Another set was used for PCL (MW 45,000, Sigma, St. Louis, Mo., USA) solution (10.0 w/w %) in dichloromethane/2-propanol (4:1 w/w) and the syringe was placed at the opposite side to the one feeding PLGA solution. The nanofibers were collected directly onto a grounded titanium Kirschner wire (K-wire, 0.5 mm diameter×9 mm length, Modern Grinding, Port Washington, Wis., USA) at a distance of 10 cm from both needle tips, over a collection time of 1 min per 0.5 mm (diameter)×9 mm (length) K-wire. The coated wires were then treated at 70° C. for 10-15 seconds. After heat treatment, the coated device was cooled to room temperature, and PCL formed a relatively smooth, uniform and uninterrupted coating on the K-wires.

Another coating configuration on non-smooth implants, such as orthopedic screws, is shown in FIG. 10. In this case, the implant was rotated at high speeds using a drill during the co-electrospinning process to produce aligned fibers prior to heat treatment at 70° C. A uniform and robust coating can be produced in this manner, which is able to withstand torque forces applied during surgery.

Results

This Example describes a presently disclosed method for applying PLGA-PCL fiber composite coating on titanium K-wires (FIG. 1A, FIG. 1B, FIG. 1C, FIG. 1D, and FIG. 1E). The implant coating was fabricated using a composite between two different polymers, PCL and PLGA. Electrospinning using a co-spinning process with two injection streams created a mixed nano-fibrous matrix of both polymers. Due to the differences in melting temperatures between the two polymers and the particularly low melting temperature of PCL, heat treatment caused PCL to melt and form a film coating over the implant while PLGA maintained a nano-fibrous matrix structure. This type of coating is biodegradable with a suitable timeframe for antibacterial treatment.

The presently disclosed coating compositions were applied to stainless steel K-wires with and without threads (FIG. 1B), showing that a conformal intact coating could be generated equally well on smooth or threaded K-wires. Therefore, it was demonstrated that the presently disclosed method is suitable for coating both smooth and textured surfaces.

The surface topography of the film was modulated by varying the ratios of the film-forming fibers and other nanofibers to obtain a composite film with either a smooth PCL film embedded with PLGA nanofibers or a film surface with nanofibers exposed on the surface to different degrees (FIG. 1C).

It was also demonstrated that more than one set of nanofibers could be incorporated in the composite film. For example, additional sets of nanofibers could be deposited onto the metallic surface by using more spinnerets or needles either in a sequential manner or concurrently via co-electrospinning. A titanium K-wire was coated with FITC loaded PLGA nanofiber following co-electrospinning of rhodamine loaded PLGA and PCL. After heat treatment, both sets of PLGA nanofibers were embedded into the PCL film. FIG. 1D illustrates a composite coating with two different sets of fibers loaded with different fluorescent dyes (FITC and rhodamine) used as a surrogate model for drug loading. There was no observed crosstalk between fibers. There was no interaction between the different layers as seen in the FITC/rhodamine images, which means additional drug layers could also be employed by spinning additional PLGA layers. This co-spinning method allows for the selective modification of the ratios of the two or more polymers being applied to the implant. Individual drug or drugs in combination can be loaded into each polymer component or fiber content.

The thickness of the composite film coating, i.e., the total weight of the film can be controlled by varying the fiber deposit time and polymer solution flow rate. FIG. 2A and FIG. 2B demonstrate that the weight of the polymer fibers and composite film coating is linearly proportional to the spinning time (FIG. 2A) and flow rate (FIG. 2B) of the polymer solution. It is therefore straightforward to control the spinning time and flow rate of the polymer solution in order to adjust the relative amount of fibers deposited on the surface of the implant.

Example 2

Loading of Antibiotics in Polymer Nanofibers and Film

Materials and Methods

The drug groups tested all included Rifampin (Rif), and the second drug was varied among linezolid (Lin), vancomycin (Van), and daptomycin (Dap). Each drug group combination of Rif and a secondary drug was tested with five pin groups as shown in Sets 1-3 (FIG. 1E). Eleven total film groups were prepared for the in vivo tests as listed in Table 1. To load the antibiotics into the polymer nanofibers or film, Rif and Lin were dissolved in corresponding 10% w/w PLGA or PCL polymer solution prior to electrospinning. Van or Dap was first dissolved in dimethyl sulfoxide (DMSO) to form a 20% (w/w) solution before being added into their respective polymer solutions to form a suspension. This suspension can be electrospun in a relatively uniform fashion. Suspensions using water as a solvent were also produced using the model drug Gentamicin (Gent). Briefly, Gent was dissolved in DI water to form a 30% (w/w) solution before being added to a PLGA solution dissolved in HFIP. The suspension was stabilized through prolonged sonication and vortexing prior to electrospinning.

The release rate of the polymer composite film was measured by HPLC. Drug release studies were conducted using coated pins created with the same loading parameters as those used for later in vivo testing (10% (w/w) drug combinations) electrospun for 60 seconds at injection rates of 0.5 mL/h from each needle. Release rate of antibiotics from the composite polymer coating was characterized by placing coated pins in 200 μL pH 7.4 PBS buffer and incubating at 37° C. in an aluminum film-covered incubator to prevent possible light-induced drug degradation. Release media was changed at fixed time points over a period of two weeks and stored in a −20° C. freezer until analysis. Drug concentrations in release media for each day were determined via reverse-phase HPLC using a C-18 column in an Alliance HPLC system and Waters 2996 PDA detector. The mobile phase was a mixture of acetonitrile and water both mixed with 0.1% TFA acid, which was run at a gradient from (15%/85%) to (40%/60%) for a total runtime of 15 minutes per sample for the elution of Van/Rif and Lin/Rif drug loading groups. Elution of the Dap/Rif loading group was conducted using a mobile phase of (49%/51%) of acetonitrile and water both mixed with 0.1% TFA acid for a total run time of 11 minutes per sample. Concentrations of the drugs were quantified using wavelengths of 343 nm for Rif, 254 nm for Lin, 280 nm for Van and 223 nm for Dap using prepared standard curves for all three drugs. As an example, FIG. 3A and FIG. 3B show the in vitro release profiles of Lin and Rif from the composite coating on titanium K-wire implants. This experiment compares PLGA fibers-PCL film composite coatings prepared with the configurations shown in FIG. 1E. FIG. 11A shows the sustained in vitro release of Gentamicin, a highly water-soluble antibiotic. Quantification was performed through the derivatization of Gentamicin with ninhydrin at 95° C. for 15 minutes and detection with a Biotek Synergy2 plate reader.

Results

As shown in FIG. 3A, the combined coating Van/Van+Rif delivered more sustained release of Van compared to Van alone or Van/Rif. The daily release of Van remained above the minimal inhibitory concentration (MIC) against *S. aureus* for 5 days and the Rif daily release (FIG. 3B) remained above the MIC for 4 days. As shown in FIG. 3C, the combined coating Lin/Lin+Rif delivered more sustained release of Lin compared to Lin alone or Lin/Rif. The daily release of Lin remained above the MIC against *S. aureus* for 14 days and the Rif daily release (FIG. 3D) remained above the MIC for ~7 days. As shown in FIG. 3E, the combined coating Dap/Dap+Rif delivered more sustained release of Dap compared to Dap alone or Dap/Rif. The daily release of Dap remained above the MIC against *S. aureus* for 7 days and the Rif daily release (FIG. 3F) remained above the MIC for ~3 days. The MIC of Gentamicin in the same bacterial strain is roughly 10 μg/mL, and this concentration could be sustained for up to 14 days as seen in FIG. 11A. The composite polymer coating allows for the co-delivery of two or more drug combinations that have different release rate profiles to optimize antimicrobial activity and biofilm prevention. The composite coating has two distinct drug release profiles characterized by fast release in PCL and slower sustained release of a second drug in PLGA. Drug release profile can be tuned by modification of polymer solutions, drug concentration, drug type, and implant surface morphology through polymer formulation and nanofiber structure. The tunable slower release of Van, Lin, and Dap combined with the faster release of Rif was by design because Rif cannot be present as a single antibiotic agent due to rapid development of Rif-resistant bacteria. Thus, the release of Van, Lin, Dap, and Gent was engineered to have a much longer and sustained release than Rif so ensure that at no time Rif was present as a single agent.

Figure 4D:
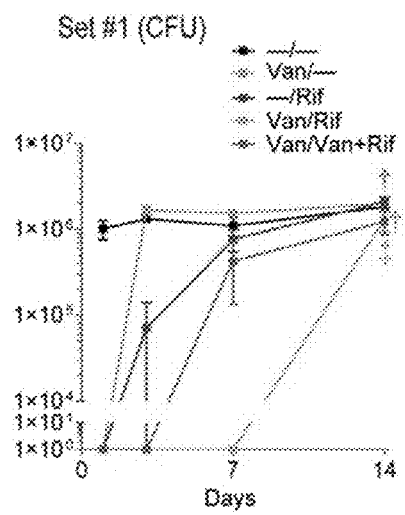
Figure 4E:
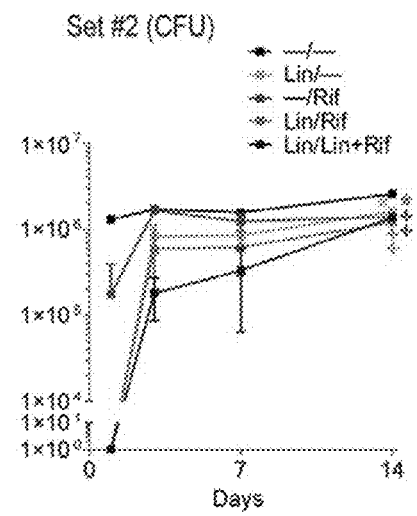
Figure 4F:
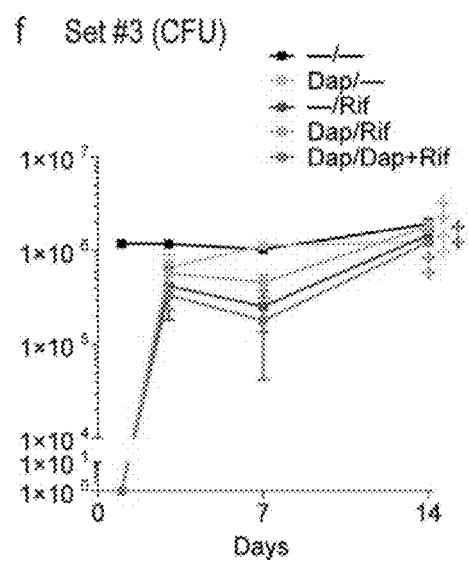

The in vitro release rates corresponded to in vitro antimicrobial activity (FIG. 4D, FIG. 4E, and FIG. 4F). The amount of released drug from the combination coatings Van/Rif, Van/Van+Rif, Lin/Rif, Lin/Lin+Rif, Dap/Rif, and Dap/Dap+Rif in the first 24 hours completely inhibited the growth of *S. aureus* bacteria in vitro. Furthermore, the amount of drug released from the coatings on day 3 in combination coatings Van/Rif, Van/Van+Rif, Lin/Lin+Rif, and Dap/Dap+Rif that delivered more sustained release of Van (FIG. 3A), Lin (FIG. 3C), and Dap (FIG. 3E), respectively, had greater inhibition of bacterial growth than the other coatings. These results suggest that the antibiotic coatings can be tuned to achieve optimized release profile for better in vitro antimicrobial activity.

Example 3

Effect of Composite Coating on In Vitro Inhibition Efficiency

Materials and Methods

A zone of inhibition assay was used as an additional assay to evaluate the in vitro release of antibiotic(s) from the composite coating. Tryptic soy agar bacterial plates were inoculated with *S. aureus* bacteria cells to yield a bacterial lawn after overnight culture. After bacterial inoculation and before culturing the plates, two identical titanium K-wires loaded with either 10 w/w % Lin, 10 w/w % Van, or 10 w/w % Dap alone, or in combination with Rif were placed in two separate areas on the plate. After culturing the plates at 37° C. for 24 hours, the antimicrobial activity of the eluded antibiotic(s) into the agar was measured as a zone of inhibition (diameter [mm]) of the bacterial growth around the K-wire.

Long-term efficacy of the antimicrobial activity was tested by storing electrospun pins at room temperature for 6 weeks, −20° C. for 6 weeks, and −80° C. for 8 months. Coated pins were protected from light during storage. These pins were then used in the same zone of inhibition assay as described hereinabove. These antimicrobial results were further confirmed with a two-week in vitro release study to determine release kinetics after storage.

Results

As shown in FIG. 4A, FIG. 4B, and FIG. 4C, the Van and Dap only coatings exhibited minimum inhibition zone when tested against *S. aureus* bacteria, suggesting that either the release of Van or Dap was too slow or the diffusion of Van or Dap was limited. Lin only coatings exhibited a much larger zone of inhibition suggesting that the release and diffusion of Lin was greater than Van or Dap. Rif containing coatings either alone or combined with the other antibiotics showed the largest zones of inhibition, but an occasional presence of colonies was observed at the outer edges of the inhibition zone. These colonies indicated that resistance had developed as seen with the Van+Rif or Dap+Rif coatings, which had bacterial colonies in the region where only the diffusion of rifampin reaches. In contrast, the combined Lin+Rif coating showed a larger zone of inhibition with no colonies seen in the inhibition zone due to the larger diffusion of Lin.

The continued efficacy of the antibiotics after storage is shown in FIG. 12A, which shows no significant loss of antimicrobial activity of Van, Lin, Dap or Rif for any of the storage conditions when compared to freshly prepared coatings. The zones of inhibition are comparable to freshly prepared controls. These results show that coatings can be prepared far in advance of surgical usage as long as they are stored with care and protected from light. In vitro release studies show that there also was no difference in the release kinetics of Van, Lin or Dap after storage as seen in FIG. 12B. The release of Rif out of the composite film coating was reduced after storage at room temperature for six weeks, but not when the pins were stored at −20° C.

Example 4

In Vivo Efficacy of the Drug Loaded Composite Coating

Materials and Methods

A previously established mouse model of a prosthetic joint infection (PJI) (Pribaz et al., 2012) was used to evaluate the efficiencies of the composite coatings in providing sustained in situ release and in vivo antimicrobial activity (FIG. 5A, FIG. 5B, FIG. 5C, FIG. 5D, FIG. 5E, FIG. 5F, FIG. 5G, FIG. 5H, FIG. 5I, FIG. 5J, FIG. 5K, and FIG. 5L). A medical-grade titanium K-wire (0.5 mm in diameter, 9 mm in length) coated with PLGA/PCL fiber coating±antibiotics was surgically placed into the right distal femur of mice. Briefly, a medial parapatellar arthrotomy on the right knee was performed with lateral displacement of the quadriceps-patellar complex. After locating the femoral intercondylar notch, the femoral intramedullary canal was manually reamed with a 25 gauge needle followed by a 23 gauge needle. The coated K-wires were then surgically placed in a retrograde fashion with 1 mm protruding into the joint space. An inoculum of the *S. aureus* bioluminescent strain Xen36 ($1\times10^3$ CFUs in 2 µL PBS) was pipetted on top of the protruding implant. The patella was relocated and the surgical incision was closed with Vicryl 5-0 sutures. For analgesia, sustained-release buprenorphine (2.5 mg/kg) was administered subcutaneously at the time of surgery.

Noninvasive and longitudinal measurements of the bacterial burden were performed using in vivo bioluminescence imaging of the bioluminescent signals from live and actively metabolizing Xen36 bacteria at the site of infection in the post-operative knee joints of anesthetized mice over a 2-week course of infection using the IVIS Lumina III in vivo imaging system (PerkinElmer) on days 0, 1, 3, 5, 7, and 14. Data are presented on a color scale overlaid on a grayscale photograph of mice and quantified as maximum radiance (photons/second/$cm^2$/steradian) within a circular region of interest ($1\times10^3$ pixels) using Living Image software. Mice were euthanized on postoperative day 14 and the peri-implant bone/joint tissue and the K-wire implants were harvested. Bacteria in the peri-implant bone/joint tissue were isolated by homogenizing bone and joint tissue from the infected knee. Bacteria adherent to the implants were detached by sonication in 1 mL 0.3% Tween 80 in tryptic soy broth (TSB) for 10 minutes followed by vortexing for 5 minutes. The number of bacterial CFU obtained from the implant and joint tissue was determined by counting CFU after an overnight culture of plates.

Biofilm formation was also confirmed using SEM analysis. Implants harvested from mice were fixed in glutaraldehyde and paraformaldehyde, post-fixed with osmium tetroxide, followed by a gradual dehydration process through ethanol and hexamethyldisilazane series. Specimens were sputter coated with gold-palladium. SEM images were obtained by using JSM-6700F system at 10 kV and 8 mm working distance.

Results

As shown in FIG. 5A, FIG. 5B, FIG. 5C, FIG. 5D, FIG. 5E, FIG. 5F, FIG. 5G, FIG. 5H, and FIG. 5I, in the combined coatings (Van/Rif, Lin/Lin+Rif, and Dap/Dap+Rif), there was substantial reduction of bacterial burden as measured by in vivo bioluminescence imaging, as well as in CFU isolated from the homogenized bone/joint tissue and isolated by sonication of the implants on day 14 after infection. Data shown revealed significantly improved in vivo bacterial clearance with combined antibiotic coatings compared to single drug coatings.

The control group and Van, Lin, or Dap only groups had increased in vivo bioluminescent signals, which peaked on day 3 and then decreased and remained above background levels. In contrast, groups that contained a combination of antibiotics with rifampin maintained near background level bioluminescent signals for all 14 days, indicating the significant reduction in bacterial burden. Colony forming unit (CFU) counting of bacterial isolated from bone/joint tissue homogenates and the implants confirmed the in vivo bioluminescence imaging results. No bacteria were found on the implants in the combined antibiotics groups by the CFU assay or by a 48-hour culture of extracts. Finally, this model was used to compare the results with the coatings to the current clinical standard-of-care practice of only using intravenous antibiotics (Osmon et al., 2013). Intravenous vancomycin prophylaxis (at equivalent the human exposure dose 110 mg/kg at −1 and 16 hours) resulted in decreased BLI signals; however the infection was not cleared as CFU were readily detected from the bone/joint tissue and the implants (FIG. 5J, FIG. 5K, and FIG. 5L).

FIG. 6A, FIG. 6B, FIG. 6C, and FIG. 6D show examples of SEM images of selected implants coated with PLGA/PCL negative control composite coating (FIG. 6A). Van-PLGA/Rif-PCL, Lin-PLGA/Lin-Rif-PCL, and Dap-PLGA/Dap-Rif-PCL composite coating (FIG. 6B, FIG. 6C, and FIG. 6D). SEM images showed *S. aureus* bacterial biofilm formation on the implants coated with PLGA/PCL (control group), along with grape-like clusters of coccoidal bacteria characteristic of *S. aureus* within the extracellular biofilm matrix. Biofilm and clusters of coccoidal bacteria were not observed on the Van-PLGA/Rif-PCL, Lin-PLGA/Lin-Rif-PCL, and Dap-PLGA/Dap-Rif-PCL groups, indicating the effectiveness of the antibiotic release system.

Finally, as the PJI progresses, there is increased bone volume that is associated with periprosthetic osteolysis and implant loosening that is a hallmark of PJIs in patients. To determine whether the antibiotic-loaded PLGA/PCL composite coatings impacted the increased bone volume, high resolution X-rays (Faxitron) were obtained at post-operative day 14 (FIG. 7A, FIG. 7B, FIG. 7C, FIG. 7D, FIG. 7E, FIG. 7F, FIG. 7G, FIG. 7H, and FIG. 7I). All PLGA/PCL coatings possessing Van, Lin or Dap plus Rif resulted in significantly decreased femur bone width and femur bone area, indicating that the combination antibiotic coatings prevented increased bone volume caused by the infection. Of note, of the single antibiotic loaded PLGA/PCL coatings, only Lin alone and Rif alone resulted in decreased femur bone width and femur bone size. These data indicate that coatings containing two antibiotics or Lin or Rif as a single agent were effective in preventing increased bone volume.

Given that osseointegration is required for the long-term performance of orthopaedic implants (Goodman et al., 2013), we determined whether the antibiotic delivery coatings impacted osseointegration by using biomechanical pull-out testing and histomorphometry. At day 14, uninfected control mice with −/− coatings had an average pull-out force of 16.4±3.8 N, whereas the presence of infection resulted in a markedly decreased average pull-out force of 4.8±1.4 N (FIG. 8). Of the best-performing coatings in vivo, Lin/Lin+ Rif and Dap/Dap+Rif coatings but not the Van/Rif coatings had pull-out forces significantly greater than −/− coatings in infected mice and similar to those of the −/− coatings in uninfected mice.

Example 5

Release Rate Kinetic of Model Drug from the Composite Coating

The near-infrared (NIR) fluorescence imaging dye indocyanine green (ICG) was used as a surrogate model for drug loading and release in an established mouse model (described in Example 4) to monitor the in vivo release kinetics from PCL coating (FIG. 9A and FIG. 9B). ICG loaded PCL was coated onto titanium K-wire (described in Example 1). The implants were surgically placed in a retrograde fashion with 1 mm protruding into the joint space of mice. The release of ICG was measured by its fluorescence intensity at different time points. It was found that the peak dissolution of ICG occurred on day 1 and the release lasted over two weeks.

Example 6

Tuning of Antibiotic Release

Various means of modulating the release of antibiotics were explored. Modifying the polymer characteristics of the PCL, PLGA or the ratio of PLGA:PCL were all viable methods of controlling the release of antibiotics. In FIG. 13A and FIG. 13B, changing the molecular weight of the PCL polymer or the thickness of the PCL electrospun layer could be used to extend the release of Rifampin from the composite coating. In this manner, release could be tuned so that Rif remains above the MIC from between 2 to 5 days. In general, increasing the coating thickness and increasing the molecular weight of the polymer both led to a longer sustained release. For PLGA, changing the ratio of the PLA:PGA blocks of the copolymer could also be used to modulate the release of antibiotics such as Gentamicin. In FIG. 11A, there is a sustained release of drug from the 50:50 PLGA whereas only a burst release was observed from the 75:25 PLGA configuration. In this manner, polymer choice can control release of Gentamicin above the MIC from between 2 to 14 days.

In combination with PLGA, the presence of the PCL film can also change the release profiles of antibiotics loaded into nanofibers. In FIG. 11B, the burst release seen for Gentamicin in PLGA nanofibers alone is reduced significantly and a more sustained linear release is achieved by loading the nanofibers into the melted PCL film layer. The PCL layer reduces the Day 1 release of Gentamicin from 80% of total loading to less than 45%.

Finally, the ratio of PLGA to PCL can control the release rate of various drug combinations. FIG. 14A shows that the ratio of PLGA to PCL can be varied from 3:1 to 1:3 and this leads to different release profiles for Van, Lin, Dap. Lin and Dap were loaded into both PCL film and PLGA nanofiber region, thus the release profile depended on the PLGA:PCL coating ratio. Because Rif is only loaded into the PCL layer, the corresponding difference in PCL thickness also can prolong or shorten the release of Rif as seen in FIG. 14B. This strategy can be used to fine-tune the final mass of each drug loaded into the composite implant coating.

Example 7

General Methods

Electrospinning to Generate a Composite Implant Coating

Poly(D,L-lactic-co-glycolic acid) (PLGA; 75:25, MW 66,000-107,000; Sigma, St. Louis, Mo.) and poly(ε-caprolactone) (PCL; MW 45,000; Sigma) solutions, each loaded with different antibiotic(s) dissolved in the solution, were electrospun onto medical-grade smooth or threaded titanium Kirschner wires (K-wires; 0.5 mm diameter×9 mm length; Modern Grinding, Port Washington, Wis.) using a co-spinning process in which two separate, opposite injection streams were sprayed simultaneously onto the implant. Polymer solutions were loaded into separate 1 mL syringes fitted with a 27-gauge blunt-end needle. High-voltage power supplies were connected to the needles through alligator clips and a voltage differential of 6-7 kV was applied between the needle and the K-wire. Two syringe pumps were used to feed the polymer solutions through the needle tips at a flow rate of 0.5 mL/h. The nanofibers were collected simultaneously and directly onto the grounded K-wire at a distance of 10 cm from both needle tips, over a collection time of 1 minute per K-wire. The coated K-wires were then heat-treated in a continuous airflow at 65-70° C. for 10-15 seconds to obtain a conformal coating. The PLGA solution (10.0 w/w % in hexafluoro-2-propanol; HFIP; Sigma) was loaded with either 1% (w/w %) linezolid (Lin; Sigma, St. Louis, Mo.), vancomycin (Van; Sigma), or daptomycin (Dap; EMD Millipore). The PCL solution (10.0 w/w % in dichloromethane/2-propanol; 4:1 w/w; Sigma) was loaded with 1% (w/w %) rifampin (Rif; Sigma) and/or Van, Lin, or Dap. Van and Dap were first dissolved in 20 $\mu$l of DMSO prior to dispersion in PCL or PLGA solutions. A composite coating on a K-wire without antibiotics was used as the negative control group (−/−). To test the effect of polymer weight ratio in the composite coating on antibiotic release, three specific PLGA/PCL composite configurations loaded with Van/Rif, Lin/Lin+Rif, and Dap/Dap+Rif, respectively, were prepared by electrospinning the same set of polymer solutions (with the same drug and polymer concentrations as described above), but the PLGA:PCL polymer weight ratio was changed from 1:1 to either 3:1 or 1:3 by adjusting the flow rates from the syringe pumps during electrospinning to 0.75 mL/h PLGA and 0.25 mL/h PCL or 3:1 PLGA/PCL coating and 0.25 mL/h PLGA and 0.75 mL/h PCL for 1:3 PLGA/PCL coating. As a result, Van loading varied with the polymer weight ratio, whereas Lin and Dap loadings were the same between these two coatings and with the 1:1 PLGA:PCL weight ratio of the coatings.

In Vitro Release Profiles of Antibiotics from the Composite Coatings

Drug release studies were conducted using coated pins created with the same loading parameters as detailed above. Release kinetics of antibiotics from the composite coating were characterized by placing coated pins in 200 μL of phosphate buffer saline (PBS, pH 7.4) at 37° C. Release media was changed daily over a period of two weeks and stored at −20° C. until analysis. Drug concentrations in release media were measured on days 1, 2, 3, 5, 7, 10 and 14 using a Waters Alliance 2690 HPLC system (Waters Corporation, Milford, Mass.) equipped with an Accucore RP-MS C18 column (100 mm×2.1 mm; Thermo Fisher Scientific) and a Waters 2996 PDA detector. The elution was carried out with a mobile phase of water and acetonitrile both mixed with 0.1% TFA at a flow rate of 1 mL/min at ambient temperature using a linear gradient elution program of 85% water to 60% acetonitrile in 15 minutes. Concentrations of the drugs were quantified using wavelengths for Van (280 nm), Lin (254 nm), Dap (224 nm) and Rif (263 nm).

Staphylococcus aureus Bioluminescent Strain

S. aureus strain Xen36 (PerkinElmer, Waltham, Mass.) previously derived from the clinical bacteremia isolate ATCC 49525 (Wright) was used in all experiments. (Francis et al., 2000). Xen36 possesses a bioluminescent construct that is integrated on a stable plasmid that is maintained in all progeny without selection. (Francis et al., 2000). Xen36 was prepared for inoculation as previously described. (Niska et al., 2013; Pribaz et al. (2012)).

In Vitro Zone of Inhibition Assay

Tryptic soy agar (TSA) bacterial plates were inoculated with S. aureus to yield a bacterial lawn after overnight culture. Before culturing the plates, two titanium K-wires each loaded with the same combination of antibiotics from each set were placed in two separate areas on the plate. After culturing at 37° C. for 24 hours, the zone of inhibition (ZOI) (diameter/mm) of bacterial growth were measured.

In Vitro Antimicrobial Activity Assay

Mid-logarithmic-phase Xen36 bacteria were prepared as above and diluted to $1 \times 10^3$ CFU/mL in Cation-Adjusted Mueller Hinton II Broth (CAMHB) (Becton Dickinson, Sparks, Md.) pH 7.3. Bacteria were then cultured 1:1 with drug release solutions collected on days 1, 3, 7 and 14 at 37° C. for 18 hours and CFU were enumerated by absorbance (A600) and a standard curve of CFU.

Mice

Ten-week-old male C57BL/6 mice were obtained from Jackson Laboratories (Bar Harbor, Me.). All animal experiments were approved by the Johns Hopkins University Animal Care and Use Committee (ACUC Protocol No. MO15M421).

Mouse Surgical Procedures for K-Wire Implantation

An established orthopaedic implant mouse model was used as previously describe. (Niska et al., 2013; Pribaz et al. (2012)). Briefly, a medial parapatellar arthrotomy on the right knee was performed and a femoral intramedullary canal was manually reamed with a 25-gauge needle followed by a 23-gauge needle. The coated K-wires were then surgically placed in a retrograde fashion with 1 mm protruding into the joint space. For experiments using the PJI model, an inoculum of Xen36 ($1 \times 10^3$ CFU in 2 μL PBS) was pipetted on top of the protruding implant before closure. Sustained-release buprenorphine (2.5 mg/kg) (ZooPharm, WY) was administered subcutaneously at the time of surgery.

In Vivo Bioluminescence Imaging

Noninvasive and longitudinal measurements of the bacterial burden were performed using in vivo bioluminescence imaging (BLI) using the Lumina III IVIS (PerkinElmer, Waltham, Mass.). Data were quantified as maximum radiance (photons/second/cm$^2$/steradian) within a circular region of interest ($1 \times 10^3$ pixels) using Living Image software (PerkinElmer, Waltham, Mass.) as previously described. (Niska et al., 2013; Pribaz et al. (2012))

Quantification of Bacteria Counts (CFU) from Bone/Joint Tissue and Implants

Mice were euthanized on day 14 and bacteria from the peri-implant bone/joint tissue and implants were isolated and enumerated as previously described. (Niska et al., 2013; Pribaz et al. (2012)). In some experiments, bone/tissue homogenates and implants were cultured in TSB at 37° C. for 48 hours in a shaking incubator at 240 rpm and plated on TSA plates to determine if the infection had been eradicated.

Scanning Electron Microscopy

K-wires were removed from the femur at 7 days after the procedure and fixed in buffered 4% formaldehyde/2.5% glutaraldehyde solution for 16 hours. All samples were post-fixed in 1% osmium tetraoxide in PBS for 2 hours, followed by subsequent dehydration in a graded ethanol series. Samples were then placed into transitional series of graded ethanol: hexamethyldisilazane (HMDS) mixtures (2:1, 1:1, 1:2; each for 30 minutes), and finally to pure HMDS (twice, 30 minutes each). Specimens were air-dried under a chemical hood before sputter-coated with a gold-palladium alloy and imaged under a field emission scanning electron microscope (SEM) (JSM-6700F FE-SEM; JEOL, Tokyo, Japan).

High-Resolution X-Ray Imaging

Mice were euthanized on postoperative day 14, and the knee joints were visualized with anteroposterior (AP) radiographs using the Faxitron MX-20 Specimen Radiography System imaging system (Faxitron Bioptics, Tucson, Ariz.). AP femur width (width in mm) was measured as the maximum femoral width in the AP radiograph and the distal cortical area (area in mm$^2$) was measured as the femoral cortical area distal to the midpoint of the K-wire using the Image J image analysis software program (http://rsbweb.nih.gov/ij/) as previously described. (Niska et al., 2013. X-rays were obtained and analyzed by an experienced orthopaedic surgeon who was blinded to the treatment groups.

μCT Imaging

Live mice were imaged postoperative day 14 within a sealed biocontainment device (Minerve, Esternay, France) as previously described. (Ordonez et al., 2015). A standard small animal anesthesia machine was used to deliver an isoflurane (Henry Schein, Melville, N.Y.) and oxygen mixture during transport and imaging. Each animal was imaged using the NanoSPECT/CT small animal imager (Bioscan, Washington, D.C.) with the following settings: x-ray tube potential 55 kVp, intensity 0.143 mA, and integration time of 1000 ms. Images were reconstructed and visualized using VivoQuant 2.50 (inviCRO, Boston, Mass.). Briefly, the femur was aligned with the vertical axis and the femoral length was measured between the center of the femoral head and the center of the femoral notch. The distal 25% of the femur was analyzed as most of the bone changes were limited to this location. In order to compensate for the limitation of the image artifacts from the titanium K-wire, a semi-automated approach of connected thresholding was used, based on voxel density measured as Hounsfield units (HU). The voxels within a range of 5,000 to 50,000 HU or 700 to 4,999 HU were selected for the titanium K-wire implant or bone region of interest (ROI), respectively. Data were analyzed by two independent personnel who were blinded to the treatments. Three-dimensional images were obtained from contoured 2D images and density measurements were reported as HU.

Statistical Analysis

Data for single comparisons were compared using a Student's t-test or Fischer's exact test (one- or two-tailed) and data for multiple comparisons were compared using a two-way ANOVA, as specifically indicated in the figure legends. All data are expressed as mean±standard error of the mean (s.e.m.). Values of $P<0.05$ were considered statistically significant.

Example 8

SUMMARY

In representative embodiments, the presently disclosed subject matter provides a biodegradable composite implant coating comprising poly(lactic-coglycolic acid) (PLGA) nanofibers embedded in a poly(ε-caprolactone) (PCL) film to deliver a tunable combination of antibiotics to adjacent tissue. In this system, the PLGA-PCL composite film forms a conformal coating on the metal implant, while two or more antibiotics can be loaded into PLGA nanofiber or PCL film separately or as a mixture. In a non-limiting, exemplary embodiment, PCL film is loaded with rifampin together with another antibiotic loaded into PLGA nanofiber or in both PCL film and PLGA fibers. The morphology and integrity of the coating, drug loading and drug release, and drug antimicrobial activity were first characterized in vitro. The efficiencies of the composite coating in providing sustained in situ release function and in vivo antimicrobial activity were evaluated using a mouse model of an orthopedic implant infection.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Ashbaugh, A G, Jiang, X, Zheng, J, Tsai, A S, Kim, W-S, Thompson, J M, Miller, R J, Shahbazian, J H, Wang, Y, Dillen, C A, Ordonez, A A, Chang, Y S, Jain, S K, Jones, J C, Sterling, R S, Mao, H-Q, Miller, L S. 2016. Polymeric nanofiber coating with tunable combinatorial antibiotic delivery prevents biofilm-associated infection in vivo. *Proceedings of the National Academy of Sciences* 113 (45) E6919-E6928.

Baddour, L. M., Y. M. Cha, and W. R. Wilson. 2012. Clinical practice. Infections of cardiovascular implantable electronic devices. *N. Engl. J. Med.* 367:842-849.

Bjarnsholt, T., O. Ciofu, S. Molin, M. Givskov, and N. Hoiby. 2013. Applying insights from biofilm biology to drug development—can a new approach be developed? *Nat. Rev. Drug Discov.* 12:791-808.

Campoccia, D., L. Montanaro, and C. R. Arciola. 2013. A review of the biomaterials technologies for infection-resistant surfaces. *Biomaterials* 34:8533-8554.

Costerton, J. W., P. S. Stewart, and E. P. Greenberg. 1999. Bacterial biofilms: a common cause of persistent infections. *Science* 284:1318-1322.

Darouiche, R. O. 2004. Treatment of infections associated with surgical implants. *N. Engl. J. Med.* 350:1422-1429.

Del Pozo, J. L. and R. Patel. 2009. Clinical practice. Infection associated with prosthetic joints. *N. Engl. J. Med.* 361:787-794.

Francis K. P., et al. 2000. Monitoring bioluminescent *Staphylococcus aureus* infections in living mice using a novel luxABCDE construct. *Infect Immun* 68:3594-3600.

Goodman, S. B., Z. Yao, M. Keeney, and F. Yang. 2013. The future of biologic coatings for orthopaedic implants. *Biomaterials* 34:3174-3183.

Hall-Stoodley, L., J. W. Costerton, and P. Stoodley. 2004. Bacterial biofilms: from the natural environment to infectious diseases. *Nat. Rev. Microbiol.* 2:95-108.

Kurtz, S. M., E. Lau, J. Schmier, K. L. Ong, K. Zhao, and J. Parvizi. 2008. Infection burden for hip and knee arthroplasty in the United States. *J. Arthroplasty* 23:984-991.

Kurtz, S., K. Ong, E. Lau, F. Mowat, and M. Halpern. 2007. Projections of primary and revision hip and knee arthroplasty in the United States from 2005 to 2030. *J. Bone Joint Surg. Am.* 89:780-785.

Kurtz, S. M., K. L. Ong, J. Schmier, F. Mowat, K. Saleh, E. Dybvik, J. Karrholm, G. Garellick, L. I. Havelin, O. Furnes, H. Malchau, and E. Lau. 2007. Future clinical and economic impact of revision total hip and knee arthroplasty. *J. Bone Joint Surg. Am.* 89 Suppl 3:144-151.

Liu, C., A. Bayer, S. E. Cosgrove, R. S. Daum, S. K. Fridkin, R. J. Gorwitz, S. L. Kaplan, A. W. Karchmer, D. P. Levine, B. E. Murray, J. Rybak, D. A. Talan, and H. F. Chambers. 2011. Clinical practice guidelines by the Infectious Diseases Society of America for the treatment of methicillin-resistant *Staphylococcus aureus* infections in adults and children. *Clin. Infect. Dis.* 52: e18-e55.

Lora-Tamayo, J., O. Murillo, J. A. Iribarren, A. Soriano, M. Sanchez-Somolinos, J. M. Baraia-Etxaburu, A. Rico, J. Palomino, D. Rodriguez-Pardo, J. P. Horcajada, N. Benito, A. Bahamonde, A. Granados, M. D. Del Toro, J. Cobo, M. Riera, A. Ramos, A. Jover-Saenz, and J. Ariza. 2013. A Large Multicenter Study of Methicillin-Susceptible and Methicillin-Resistant *Staphylococcus aureus* Prosthetic Joint Infections Managed with Implant Retention. *Clin. Infect. Dis.* 56:182-194.

Niska J. A., et al. 2012. Daptomycin and tigecycline have broader effective dose ranges than vancomycin as prophylaxis against a *Staphylococcus aureus* surgical implant infection in mice. *Antimicrob Agents Chemother* 56(5): 2590-2597.

Ordonez A. A., et al. 2015. Radioiodinated DPA-713 imaging correlates with bactericidal activity of tuberculosis treatments in mice. *Antimicrob Agents Chemother* 59(1): 642-649.

Osmon, D. R., E. F. Berbari, A. R. Berendt, D. Lew, W. Zimmerli, J. M. Steckelberg, N. Rao, A. Hanssen, and W. R. Wilson. 2013. Diagnosis and management of prosthetic joint infection: clinical practice guidelines by the Infectious Diseases Society of America. *Clin. Infect. Dis.* 56: e1-e25.

Pribaz, J. R., N. M. Bernthal, F. Billi, J. S. Cho, R. I. Ramos, Y. Guo, A. L. Cheung, K. P. Francis, and L. S. Miller. 2012. Mouse model of chronic post-arthroplasty infection: noninvasive in vivo bioluminescence imaging to monitor bacterial burden for long-term study. *J. Orthop. Res.* 30:335-340.

Raad, I., H. Hanna, Y. Jiang, T. Dvorak, R. Reitzel, G. Chaiban, R. Sherertz, and R. Hachem. 2007. Comparative activities of daptomycin, linezolid, and tigecycline against catheter related methicillin-resistant *Staphylococcus* bacteremic isolates embedded in biofilm. *Antimicrob. Agents Chemother.* 51:1656-1660.

Saginur, R., M. Stdenis, W. Ferris, S. D. Aaron, F. Chan, C. Lee, and K. Ramotar. 2006. Multiple combination bactericidal testing of staphylococcal biofilms from implant associated infections. *Antimicrob. Agents Chemother.* 50:55-61.

Sandoe, J. A., G. Barlow, J. B. Chambers, M. Gammage, A. Guleri, P. Howard, E. Olson, J. D. Perry, B. D. Prendergast, M. J. Spry, R. P. Steeds, M. H. Tayebjee, and R. Watkin. 2015. Guidelines for the diagnosis, prevention and management of implantable cardiac electronic device infection. Report of a joint Working Party project on behalf of the British Society for Antimicrobial Chemotherapy (BSAC, host organization), British Heart Rhythm Society (BHRS), British Cardiovascular Society (BCS), British Heart Valve Society (BHVS) and British Society for Echocardiography (BSE). *J. Antimicrob. Chemother.* 70:325-359.

Senneville, E., D. Joulie, L. Legout, M. Valette, H. Dezeque, E. Beltrand, B. Rosele, T. d'Escrivan, C. Loiez, M. Caillaux, Y. Yazdanpanah, C. Maynou, and H. Migaud. 2011. Outcome and predictors of treatment failure in total hip/knee prosthetic joint infections due to *Staphylococcus aureus*. *Clin. Infect. Dis.* 53:334-340.

Zimmerli, W., A. Trampuz, and P. E. Ochsner. 2004. Prosthetic-joint infections. *N. Engl. J. Med.* 351:1645-1654.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for coating an implantable medical device with a conformal coating comprising at least a first bioactive agent and a second bioactive agent, the method comprising:
   (a) depositing onto at least a portion of a metallic surface of an implantable medical device using electrospinning:
      (i) a plurality of polymer nanofibers, wherein the plurality of polymer nanofibers comprise at least a first set of polymer nanofibers with a melting temperature of about 40° C. to about 100° C. and at least a second set of polymer nanofibers with a higher melting temperature than the melting temperature of the first set of polymer nanofibers; and
      (ii) at least a first bioactive agent loaded into the first set of polymer nanofibers and a second bioactive agent loaded into the second set of polymer nanofibers;
   (b) annealing the implantable medical device for a controlled time period at a controlled temperature that is higher than the melting temperature of the first set of polymer nanofibers, but lower than the melting temperature of the second set of polymer nanofibers; and
   (c) cooling the implantable device to form a conformal coating comprising: (i) a polymer film comprising the first bioactive agent; and (ii) the second set of polymer nanofibers comprising the second bioactive agent embedded therein, and wherein:
   the first bioactive agent has a first release rate in vivo and the second bioactive agent has a second release rate in vivo, wherein the first release rate of the first bioactive agent in vivo from the polymer film is independent of the second release rate of the second bioactive agent in vivo from the second set of polymer nanofibers.

2. The method of claim 1, wherein annealing the implantable medical device occurs at a controlled temperature that is from about 10° C. to about 20° C. higher than the melting temperature of the first set of polymer nanofibers.

3. The method of claim 1, wherein the annealing step does not reduce the bioactivity of the first bioactive agent and the second bioactive agent.

4. The method of claim 1, wherein the weight percentage of the first bioactive agent in the first set of polymer nanofibers and the weight percentage of the second bioactive agent in the second set of polymer nanofibers is from about 1% to about 50%.

5. The method of claim 1, wherein the controlled time period is from about 10 seconds to about 20 minutes.

6. The method of claim 1, further comprising at least a third set of polymer nanofibers, wherein the polymer film is loaded with the first bioactive agent, the second set of polymer nanofibers is loaded with the second bioactive agent, and the third set of polymer nanofibers is loaded with at least a third bioactive agent, wherein the first bioactive agent, the second bioactive agent, and the third bioactive agent are each different bioactive agents.

7. The method of claim 1, wherein the conformal coating releases the first bioactive agent and the second bioactive agent simultaneously and in a controlled manner, wherein the first bioactive agent is released from the polymer film and the second bioactive agent is released from the second set of polymer nanofibers.

8. The method of claim 1, wherein the conformal coating releases the first bioactive agent and the second bioactive agent simultaneously and immediately in a controlled manner, wherein the first bioactive agent is released from the polymer film and the second bioactive agent is released from the second set of polymer nanofibers.

9. The method of claim 1, wherein the conformal coating releases the first bioactive agent and the second bioactive agent simultaneously and immediately at different release rates in a controlled manner.

10. The method of claim 1, wherein the conformal coating releases the first bioactive agent and the second bioactive agent simultaneously and immediately at different release rates in a controlled manner, wherein the first bioactive agent is released from the polymer film and the second bioactive agent is released from the second set of polymer nanofibers.

11. The method of claim 6, wherein the conformal coating releases the first bioactive agent, the second bioactive agent, and/or the third bioactive agent over a time period of about three days to about four weeks.

12. The method of claim 6, wherein the first set of polymer nanofibers, the second set of polymer nanofibers, and the third set of polymer nanofibers each comprise a different homopolymer or copolymer.

13. The method of claim 6, wherein the first set of polymer nanofibers, the second set of polymer nanofibers, and the third set of polymer nanofibers each comprise a homopolymer or copolymer of monomers selected from the group consisting of ε-caprolactone, D-lactide, L-lactide, and glycolide.

14. The method of claim 1, wherein the first set of polymer nanofibers comprises poly(ε-caprolactone).

15. The method of claim 1, wherein the second set of polymer nanofibers comprises poly(D,L-lactide-co-glycolide).

16. The method of claim 1, wherein the first set of polymer nanofibers comprises a polymer that is selected from the group consisting of poly(ε-caprolactone), a copolymer of ε-caprolactone and D-lactide, a copolymer of ε-caprolactone and L-lactide, and a copolymer of ε-caprolactone and glycolide.

17. The method of claim 1, wherein the first set of polymer nanofibers comprises poly(ε-caprolactone), and the second set of polymer nanofibers comprises poly(D,L-lactide-co-glycolide).

18. The method of claim 1, wherein the first bioactive agent and the second bioactive agent are each an antibiotic.

19. The method of claim 18, wherein the antibiotic is selected from the group consisting of rifampin, linezolid, vancomycin and daptomycin.

20. The method of claim 1, wherein
(1) the first bioactive agent is linezolid and rifampin, and the second bioactive agent is linezolid; or
(2) the first bioactive agent is daptomycin and rifampin, and the second bioactive agent is daptomycin; or
(3) the first bioactive agent is rifampin, and the second bioactive agent is vancomycin.

21. The method of claim 1, wherein the plurality of nanofibers have an average diameter from about 50 nm to about 10 µm.

22. The method of claim 1, wherein the polymer film has an average thickness from about 20 µm to about 500 µm.

23. The method of claim 1, wherein the coating is biodegradable.

24. The method of claim 1, wherein the weight ratio of the at least second set of polymer nanofibers and the polymer film is from about 80:20 to about 10:90.

25. The method of claim 17, wherein the weight ratio of poly(D,L-lactide-co-glycolide) to poly(ε-caprolactone) is from about 80:20 to about 10:90.

26. The method of claim 1, wherein the polymer film further comprises hydroxyapatite nanocrystals.

27. The method of claim 1, wherein the annealing occurs at a controlled temperature that is from about 50° C. to about 80° C.

28. The method of claim 1, wherein the first bioactive agent and the second bioactive agent are selected from the group consisting of a polypeptide, growth factor, a steroid agent, a therapeutic antibody, an antibody fragment, a DNA, an RNA, and siRNA, an antimicrobial agent, an antibiotic, an anti-retroviral agent, an anti-inflammatory agent, an anti-tumor agent, anti-angiogenic agent, and a chemotherapeutic agent.

29. The method of claim 1, wherein the implantable medical device is an orthopedic device, a dental device, a cardiovascular device, a neurological device, a neurovascular device, a gastrointestinal device, a muscular device, an intramedullary device, or an ocular device.

30. The method of claim 1, wherein the implantable medical device is an artificial joint, an internal fracture-fixation device, an external fracture-fixation device, a device for fixation of small bones, a device for fixation of the spine, a pacemaker, an implantable cardioverter-defibrillator, a stent, a nail, a rod, a screw, a plate, a clip, or a pin.

31. The method of claim 1, wherein the conformal coating inhibits at least one genus of bacteria.

32. The method of claim 31, wherein the genus of bacteria is selected from the group consisting of *Staphylococcus, Acinetobacter, Klebsiella, Enterococcus, Streptococcus, Escherichia, Proteus, Pseudomonas, Propionibacterium* and *Vibrio*.

* * * * *